(12) United States Patent
Bravo de la Parra et al.

(10) Patent No.: US 10,793,611 B2
(45) Date of Patent: Oct. 6, 2020

(54) BACILLUS THURINGIENSIS CYT1A MUTANTS

(71) Applicant: Universidad Nacional Autónoma de México, Mexico City (MX)

(72) Inventors: Maria Alejandra Bravo de la Parra, Cuernavaca Morelos (MX); Mario Soberón Chavez, Cuernavaca Morelos (MX)

(73) Assignee: Universidad Nacional Autónoma de México, Mexico City (MX)

( * ) Notice: Subject to any disclaimer, the term of this patent is extended or adjusted under 35 U.S.C. 154(b) by 0 days.

(21) Appl. No.: 16/302,261

(22) PCT Filed: Apr. 18, 2017

(86) PCT No.: PCT/IB2017/000510
§ 371 (c)(1),
(2) Date: Nov. 16, 2018

(87) PCT Pub. No.: WO2017/199078
PCT Pub. Date: Nov. 23, 2017

(65) Prior Publication Data
US 2019/0185521 A1 Jun. 20, 2019

Related U.S. Application Data

(60) Provisional application No. 62/337,656, filed on May 17, 2016.

(51) Int. Cl.
*A61K 38/00* (2006.01)
*C07K 14/325* (2006.01)
*A01N 63/10* (2020.01)

(52) U.S. Cl.
CPC ............ *C07K 14/325* (2013.01); *A01N 63/10* (2020.01)

(58) Field of Classification Search
None
See application file for complete search history.

(56) References Cited

U.S. PATENT DOCUMENTS

2015/0148288 A1  5/2015  Kennedy et al.

FOREIGN PATENT DOCUMENTS

WO   WO-2010/077672 A2   7/2010
WO   WO-2017/199078 A2   11/2017

OTHER PUBLICATIONS

Promodonkoy, 2008, Journal of Biotechnology, 133, 287-293 (Year: 2008).*
Lopez-Diaz, et al., "Oligomerization is a key step in Cyt1Aa membrane insertion and toxicity but not necessary to synergize Cry11Aa toxicity in Aedes aegypti larvae", Environmental Microbiology, 2013, vol. 15, No. 11, pp. 3030-3039.
Promdonkoy, B., et al. 2008. Amino acid substitutions in αA and αC of Cyt2Aa2 alter hemolytic activity and mosquito-larvicidal specificity. J. Biotechnol. 133, 287-293.
International Search Report and Written Opinion dated Dec. 19, 2017 by the International Searching Authority for International Application No. PCT/IB2017/000510, filed on Apr. 18, 2017 and published as WO 2017/199078 on Nov. 23, 2017 (Applicant-Universidad Nacional Autonoma de Mexico) (10 Pages).
International Preliminary Report on Patentability dated Nov. 20, 2018 by the International Searching Authority for International Application No. PCT/IB2017/000510, filed on Apr. 18, 2017 and published as WO 2017/199078 on Nov. 23, 2017 (Applicant-Universidad Nacional Autonoma de Mexico)(6 Pages).

* cited by examiner

*Primary Examiner* — Satyanarayana R Gudibande
(74) *Attorney, Agent, or Firm* — Ballard Spahr LLP

(57) ABSTRACT

The disclosure provides nucleic acids encoding variant polypeptides having pesticidal activity against insect pests, including Lepidoptera and Diptera. Particular embodiments provide isolated nucleic acids encoding Cyt1A variant polypeptides, pesticidal compositions, DNA constructs, and transformed microorganisms and plants comprising a nucleic acid of the embodiments. These compositions find use in methods for controlling pests, particularly Diptera pests.

20 Claims, 4 Drawing Sheets

Specification includes a Sequence Listing.

FIG. 1

```
                1                                                    50
Cyt1Aa    (1)   --------MEN-----LNHCPLEDIKVNPWKTPQSTARVITLRVEDPNEI
Cyt1Ab    (1)   --------MEN-----PNHCPLEDIQVNPWKTPQSKARVITLRIDDPNEI
Cyt1Ba    (1)   MKESIYYNEENEIQISQGNEFPEELGHNPWROPQSTARVIYLKVKDPIDT
Cyt2Aa    (1)   -----------MYTKNFSNSRMEVKGNNGCSAPIIRKPFKHIVLTVPSSD
Cyt2Bb    (1)   -----------MYTKNLNSL--EINEDYQYSRPIIKKPFHITLTVPSSD
Cyt2Ba    (1)   --------MHLNNLNNFNNL--ENNGEYHCSGPIIKKPFRHIALTVPSSD
Cyt2Bc    (1)   -----------MYINNFDFP--EKNNDYQCSGPIIKKPFRHIALTVPSSD 51                                                  100
Cyt1Aa   (38)   NNLLSINETDNPNYILQAIMLANAFQNALVPTSEDFG-DALRFSLPKGLE
Cyt1Ab   (38)   NNLLSINETNTNYLLQAIMLANAFQKALVPTSEEFAEDALQFSLTKGLE
Cyt1Ba   (51)   TQLLEITELNPNYVIQAIQLAAFQDALVPTEEFG-DALRFSLPKGLE
Cyt2Aa   (40)   LDNFNTVFYVQPQYINQALHLANAFQGAIDPLNLNFN-------FEKALQ
Cyt2Bb   (38)   IASFNEIFYLEPQYVAQALRLTNTFQAAIDPLTLNFD-------FEKALQ
Cyt2Ba   (41)   ITNFNEIFYVEPQYIAQAIRLTNTFQGAIDPLTLNFN-------FEKALQ
Cyt2Bc   (38)   ITNFNEIFYVEPQYIAQAIRLTNTFQGAIDPLTLNFN-------FEKALQ 101                                                 150
Cyt1Aa   (87)   IANLITPMGAVVSIVDQNVTQNNQVSVMINKVIEVLKIVLGVALSGS-V
Cyt1Ab   (88)   VANLISPPGAVVQIVDQNVSQTNNQVSAMINKVIDVLKSILGVALGQS-V
Cyt1Ba  (100)   VAKLIQPKGAVVATTQTLSQSNNQVSVMIDKVISVLKIVMGVALSGS-I
Cyt2Aa   (83)   IANGI-PNSAIVKTLNQSVIQQTVEISVMEQLKKIIQEVLGLVINSTSF
Cyt2Bb   (81)   IANGL-PNAGITGTLNQSVIQQTIEISVMISQIKEIIRNVLGLVINSTNF
Cyt2Ba   (84)   IANGL-PNAGVTGTINQSVIHQTIEVSVMISQIKEIIRSVLGLVINSANF
Cyt2Bc   (81)   IANGL-PNAGVTGTLNQSVIHQTIEISVMISQIKEIIRSVLGLVINSANF 151                                                 200
Cyt1Aa  (136)   IDQLIAAVTNTFTNLNQQKNEAWIFWGKETANQTIYTYNVLFAIQNAQTG
Cyt1Ab  (137)   IEQLISAVTNTFTNLNQQKNEAWIFWGRETSTQTIYTYNVLFAIQNGQTG
Cyt1Ba  (149)   ITQLIAAITDTFTNLNIQQDSIWVEWGKETSHQTIYTYNVMFAIQNETTG
Cyt2Aa  (132)   WNSVEATIKGTFTNLDTQIDEAWIFWHSLSAHNTSYYYNILFSIQNEDTG
Cyt2Bb  (130)   WNSVLAAITNTFTNLEPQVDENWIVWRNLSATHTSYYYKILFSIQNEDTG
Cyt2Ba  (133)   WNSVVSAITNTFTNLEPQVDENWIVWRNLSATQTSYFYKILFSIQNEDTG
Cyt2Bc  (130)   WNNVVSAITNTFTNLEPQVDENWIVWRNLSANQTSYYYKILFSIQNEDTG 201                                                 250
Cyt1Aa  (186)   GVMYCVPVGFEIKVSAVKEQVLFFTIQDSASYNVIIQSLKFAQPLVSSSQ
Cyt1Ab  (187)   GVMYCVPVGFEIKVSAVKERVLFLTIQDSASYNVIIQSLKTAQPLVSASE
Cyt1Ba  (199)   RVMMCVPIGFEIRVFTDKRTVLFLTTKDYANYSVIIQDLRFAQELIDSRA
Cyt2Aa  (182)   AVMAVLPLAFEVSVDVEKQKVLFFTIKDSARYEVKMKALTLVQALHSSN-
Cyt2Bb  (180)   AFMAVLPIAFEITVDVQKQQLLFITIRDSARYEVKMKALTVVQLLDSYN-
Cyt2Ba  (183)   RFMAILPIAFEITVDVQKQQLLFITIKDSARYEVKMKALTVVQALDSYN-
Cyt2Bc  (180)   RFMAVLPIAFEINVDVHKQQLLFITIKDSARYEVKMKALTVVQALDSYN-
```

FIG. 1, cont'd

```
           251                                  285
Cyt1Aa  (236) YPIADLISAINGIL--------------------
Cyt1Ab  (237) YPIADLISAINGIL--------------------
Cyt1Ba  (249) LSINDLSEARSSKYLY------------------
Cyt2Aa  (231) APIVDIFNVNNYNLYHS---NHKIIQNLNLSN---
Cyt2Bb  (229) APIIDVFNVHNYGLYQSNHPNHHILQNLNLNKIKG
Cyt2Ba  (232) APIIDVFNVRNYSLHR---PNHNILQNLNVNPIKS
Cyt2Bc  (229) APIIDVFNIHNYSLHR---PNYHILQNLNVNPIKS
```

FIG. 2

```
                                              β0           β1
                                       EEEEEEEEEEE     EEEEE    HH
                              1                                       50
    Cyt1Aa      (1)  MENLNHCPLEDIKVNPWKTPQSTARVITLRVEDPNEINNLLSINEIDNPN
    Cyt1Aa A59C (1)  MENLNHCPLEDIKVNPWKTPQSTARVITLRVEDPNEINNLLSINEIDNPN
    Cyt1Aa A61C (1)  MENLNHCPLEDIKVNPWKTPQSTARVITLRVEDPNEINNLLSINEIDNPN

α1          β2        β3       α2
                         HHHHHHHHHHHHHHHHHEEE    EEE  HHHHHHHHH    EEEEEE
                              51    * *                                 100
    Cyt1Aa     (51)  YILQAIMLANAFQNALVPTSTDFGDALRFSMPKGLEIANTITPMGAVVSY
    Cyt1Aa A59C(51)  YILQAIMLCNAFQNALVPTSTDFGDALRFSMPKGLEIANTITPMGAVVSY
    Cyt1Aa A61C(51)  YILQAIMLANCFQNALVPTSTDFGDALRFSMPKGLEIANTITPMGAVVSY

β4           α3             α4       α5
                         EEEEEEEEEEEHHHHHHHHHHHHHHHHH HHHHHH HHHHHHHHHHH
                              101                                       150
    Cyt1Aa     (101) VDQNVTQTNNQVSVMINKVLEVLKTVLGVALSGSVIDQLTAAVTNTFTNL
    Cyt1Aa A59C(101) VDQNVTQTNNQVSVMINKVLEVLKTVLGVALSGSVIDQLTAAVTNTFTNL
    Cyt1Aa A61C(101) VDQNVTQTNNQVSVMINKVLEVLKTVLGVALSGSVIDQLTAAVTNTFTNL

β5           β6                 β7
                         EEEEEEEE     EEEEEEEEEEEEE    EEEEEEEEEEEEEE
                              151                                       200
    Cyt1Aa     (151) NTQKNEAWIFWGKETANQTNYTYNVLFAIQNAQTGGVMYCVPVGFEIKVS
    Cyt1Aa A59C(151) NTQKNEAWIFWGKETANQTNYTYNVLFAIQNAQTGGVMYCVPVGFEIKVS
    Cyt1Aa A61C(151) NTQKNEAWIFWGKETANQTNYTYNVLFAIQNAQTGGVMYCVPVGFEIKVS

α6          β8
                         HHHH      EEEEEEEEEEEEEEEE
                              201                                       249
    Cyt1Aa     (201) AVKEQVLFFTIQDSASYNVNIQSLKFAQPLVSSSQYPIADLTSAINGTL
    Cyt1Aa A59C(201) AVKEQVLFFTIQDSASYNVNIQSLKFAQPLVSSSQYPIADLTSAINGTL
    Cyt1Aa A61C(201) AVKEQVLFFTIQDSASYNVNIQS

BACILLUS THURINGIENSIS CYT1A MUTANTS

CROSS REFERENCE TO RELATED APPLICATIONS

This application is a U.S. National Phase application based on International Patent Application No. PCT/IB2017/000510, filed on Apr. 18, 2017, which claims benefit of U.S. Provisional Application No. 62/337,656, filed on May 17, 2016, the entire contents of both applications are hereby incorporated by reference.

REFERENCE TO SEQUENCE LISTING SUBMITTED ELECTRONICALLY

A sequence listing having the file name "36446_0342U2_Sequence_Listing.txt" created on Oct. 22, 2018, and having a size of 41,079 bytes is filed in computer readable form concurrently with the specification. The sequence listing is part of the specification and is herein incorporated by reference in its entirety pursuant to 37 C.F.R. § 1.52(e)(5).

FIELD

The present disclosure relates to recombinant nucleic acids that encode pesticidal polypeptide variants characterized by pesticidal activity against insect pests. Compositions and methods of the invention utilize the disclosed nucleic acids, and their encoded pesticidal polypeptides, to control plant pests.

BACKGROUND

Insect pests are a major factor in the loss of the world's agricultural crops. For example, western corn rootworm, northern corn rootworm, southern corn rootworm and Mexican corn rootworm can be economically devastating to agricultural producers. Insect pest-related crop loss from corn rootworm attacks on field and sweet corn alone has reached about one billion dollars a year in damage and control expenses. Vector-borne diseases caused by the transmission of pathogens and parasites from one infected person (or animal) to another, cause serious diseases in human populations. Mosquito-borne diseases are a rapidly growing human and domestic animal public health problem in many parts of the world. The female mosquito of the genus *Anopheles* carries the malaria parasite. Worldwide, malaria is a leading cause of premature mortality, particularly in children under the age of five, with an estimated 207 million cases and more than half a million deaths in 2012. A large share of the world population is at risk Dengue fever, a viral infection transmitted by the *Aedes aegypti* mosquito, as over 2.5 billion people live in affected areas. The annual number of dengue infections is estimated at 50 to 100 million and over the last 50 years has shown a 30-fold increase in disease incidence. The economic cost of this disease has been estimated to be at least $1.8 billion yearly. Traditionally, the primary method for impacting insect pest populations is the application of broad-spectrum chemical insecticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is need to develop alternative biopesticides.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including Lepidoptera, Diptera, Coleoptera, Hemiptera, and others. *Bacillus thuringiensis* (Bt) and *Bacillus papilliae* are among the most successful biocontrol agents discovered to date. Insect pathogenicity has also been attributed to strains of *B. larvae, B. lentimorbus, B. sphaericus* (Harwook, ed., ((1989) *Bacillus* (Plenum Press), 306) and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial insecticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants have been genetically engineered to produce pesticidal proteins isolated from strains of Bt (see, e.g., Aronson (2002) *Cell Mol. Life Sci.* 59(3):417-425; Schnepf et al. (1998) *Microbiol Mol Biol Rev.* 62(3):775-806). These genetically engineered crops are now widely used in American agriculture and have provided the farmer with an environmentally friendly alternative to traditional insect-control methods. In addition, potatoes genetically engineered to contain pesticidal Cry toxins have been sold to the American farmer. While they have proven to be very successful commercially, these genetically engineered, insect-resistant crop plants provide resistance to only a narrow range of the economically important insect pests.

Accordingly, there remains a need for new Bt toxins with a broader range of insecticidal activity against insect pests, e.g., toxins which are active against a greater variety of insects from the orders Lepidoptera and Diptera. In addition, there remains a need for biopesticides having activity against a variety of insect pests and for biopesticides which have improved properties including increased insecticidal activity and reduced hemolytic activity.

SUMMARY

Compositions and methods are provided for impacting insect pests. More specifically, the embodiments of the present invention relate to methods of impacting insects utilizing nucleotide sequences encoding insecticidal peptides to produce transformed microorganisms and plants that express an insecticidal polypeptide of the embodiments. In some embodiments, the nucleotide sequences encode polypeptides that are pesticidal for at least one insect belonging to the order Lepidoptera.

The embodiments provide nucleic acid molecules, fragments and variants thereof which encode polypeptides (e.g. SEQ ID NO: 3 and SEQ ID NO: 5 encoding SEQ ID NO: 4 and SEQ ID NO: 6 respectively) that possess improved activity compared to Cyt1Aa (SEQ ID NO: 2).

The embodiments provide isolated pesticidal (e.g., insecticidal) polypeptides encoded by a modified (e.g., mutagenized or manipulated) nucleic acid of the embodiments. In particular examples, Cyt1A variant polypeptides of the embodiments include fragments of full-length proteins and polypeptides that are produced from mutagenized nucleic acids designed to introduce particular amino acid sequences into the polypeptides of the embodiments. In particular embodiments, the polypeptides have enhanced pesticidal activity relative to the activity of the naturally occurring polypeptide from which they are derived. In particular embodiments, the polypeptides have decreased hemolytic activity relative to the activity of the naturally occurring polypeptide from which they are derived.

The nucleic acids of the embodiments can also be used to produce transgenic (e.g., transformed) monocot or dicot plants that are characterized by genomes that comprise at least one stably incorporated nucleotide construct comprising a coding sequence of the embodiments operably linked to a promoter that drives expression of the encoded pesticidal polypeptide. Accordingly, transformed plant cells, plant tissues, plants, and seeds thereof are also provided.

In a particular embodiment, a transformed plant can be produced using a nucleic acid that has been optimized for increased expression in a host plant. For example, one of the pesticidal polypeptides of the embodiments can be back-translated to produce a nucleic acid comprising codons optimized for expression in a particular host, for example a crop plant such as a corn (*Zea mays*) plant. Expression of a coding sequence by such a transformed plant (e.g., dicot or monocot) will result in the production of a pesticidal polypeptide and confer increased insect resistance to the plant. Some embodiments provide transgenic plants expressing pesticidal polypeptides that find use in methods for impacting various insect pests.

The embodiments further include pesticidal or insecticidal compositions containing the insecticidal polypeptides of the embodiments, and can optionally comprise further insecticidal peptides. The embodiments encompass the application of such compositions to the environment of insect pests in order to impact the insect pests.

BRIEF DESCRIPTION OF THE DRAWINGS

FIG. 1 shows an AlignX™ amino acid sequence alignment of the Cyt1 and Cyt2 family members: Cyt1Aa (SEQ ID NO: 2), Cyt1Ab (SEQ ID NO: 7), Cyt1Ba (SEQ ID NO: 8), Cyt2Aa (SEQ ID NO: 9), Cyt2Ba (SEQ ID NO: 10), Cyt2Bb (SEQ ID NO: 11), and Cyt1Bc (SEQ ID NO: 12). The sequence diversity is highlighted.

FIG. 2 shows an AlignX™ amino acid sequence alignment of of Cyt1Aa (SEQ ID NO: 2), Cyt1Aa A59C variant polypeptide (SEQ ID NO: 4), Cyt1Aa A61C variant polypeptide (SEQ ID NO: 6). The amino acid substitution in Cyt1Aa A59C variant polypeptide (SEQ ID NO: 4) and Cyt1Aa A61C variant polypeptide (SEQ ID NO: 6) is highlighted and underlined, and the position is indicated by an "*" above the residue. The Cyt1Aa (SEQ ID NO: 2) secondary structure elements are labeled above the corresponding sequence; β-strands of are depicted by an "E" and α-helices are depicted by an "H". Adapted from Cohen S. et al., *Journal of Molecular Biology* 413: 804-814 (2011).

DETAILED DESCRIPTION

Figure 3:
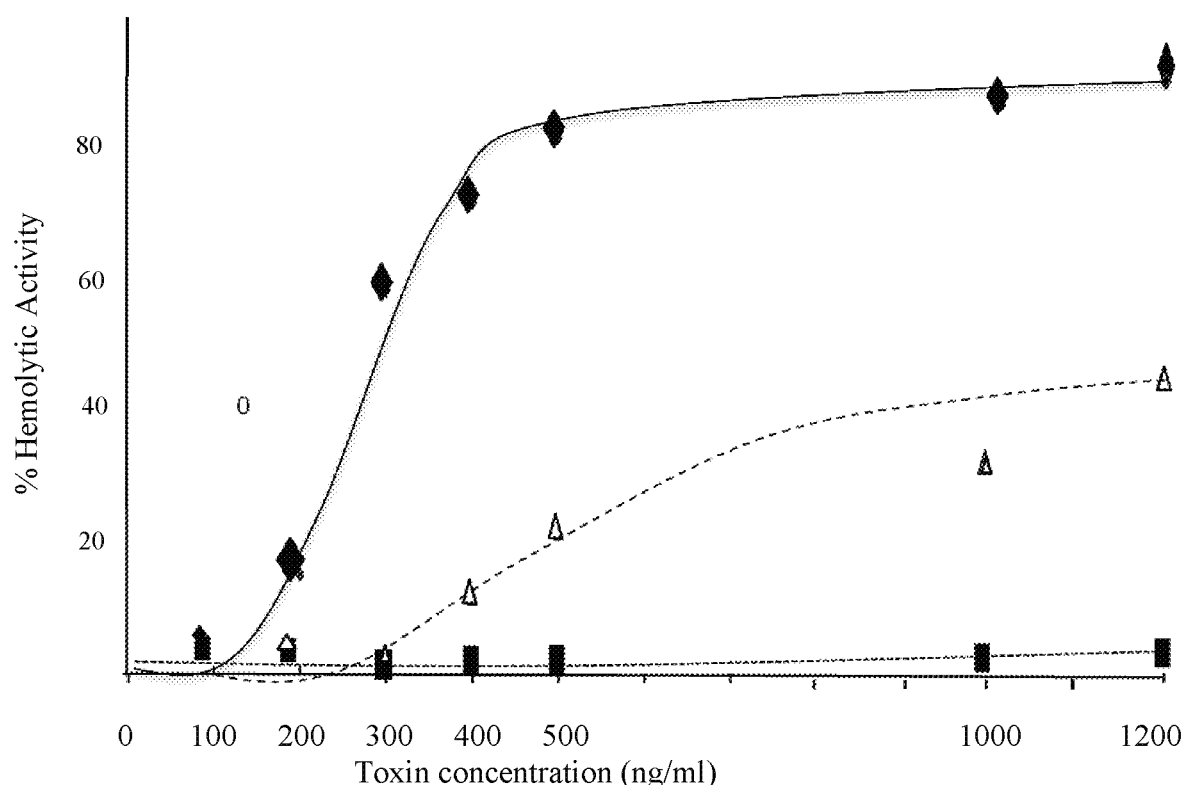
FIG. 3 shows the hemolytic activity of Cyt1Aa, SEQ ID NO: 2, (♦—Cyt1Aa); Cyt1Aa A59C, SEQ ID NO: 4, (■—A59C); and Cyt1Aa A61C, SEQ ID NO: 6 (Δ—A61C). The hemolysis of rabbit red blood cells is plotted as % hemolytic activity versus protein concentration.

The embodiments of the invention are drawn to compositions and methods for impacting insect pests, particularly plant pests. More specifically, the isolated nucleic acid of the embodiments, and fragments and variants thereof, comprise nucleotide sequences that encode pesticidal polypeptides (e.g., proteins). The disclosed Cyt1A variant polypeptides are biologically active (e.g., pesticidal) against insect pests such as, but not limited to, insect pests of the order Coleoptera.

The compositions of the embodiments comprise isolated nucleic acids, and fragments and variants thereof, which encode pesticidal polypeptides, expression cassettes comprising nucleotide sequences of the embodiments, isolated Cyt1A variant polypeptides, and pesticidal compositions. Some embodiments provide modified pesticidal polypeptides characterized by improved insecticidal activity against Coleopterans relative to the pesticidal activity of the corresponding wild-type protein. The embodiments further provide plants and microorganisms transformed with these novel nucleic acids, and methods involving the use of such nucleic acids, pesticidal compositions, transformed organisms, and products thereof in impacting insect pests.

The nucleic acids and nucleotide sequences of the embodiments may be used to transform any organism to produce the encoded Cyt1A variant polypeptides. Methods are provided that involve the use of such transformed organisms to impact or control plant pests. The nucleic acids and nucleotide sequences of the embodiments may also be used to transform organelles such as chloroplasts (McBride et al. (1995) *Biotechnology* 13: 362-365; and Kota et al. (1999) *Proc. Natl. Acad. Sci. USA* 96: 1840-1845).

The embodiments further relate to the identification of fragments and variants of the naturally-occurring coding sequence that encode biologically active Cyt1A variant polypeptides. The nucleotide sequences of the embodiments find direct use in methods for impacting pests, particularly insect pests such as pests of the order Lepidoptera. Accordingly, the embodiments provide new approaches for impacting insect pests that do not depend on the use of traditional, synthetic chemical insecticides. The embodiments involve the discovery of naturally-occurring, biodegradable pesticides and the genes that encode them.

The embodiments further provide fragments and variants of the naturally occurring coding sequence that also encode biologically active (e.g., pesticidal) polypeptides. The nucleic acids of the embodiments encompass nucleic acid or nucleotide sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. The embodiments further provide mutations which confer improved or altered properties on the polypeptides of the embodiments. See, e.g. U.S. Pat. No. 7,462,760.

In the description that follows, a number of terms are used extensively. The following definitions are provided to facilitate understanding of the embodiments.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to that of naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a protein of the embodiments can be produced by expression of a recombinant nucleic acid of the embodiments in an appropriate host cell, or alternatively by a combination of ex vivo procedures.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

An "isolated" nucleic acid is generally free of sequences (such as, for example, protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

As used herein, the term "isolated" or "purified" as it is used to refer to a polypeptide of the embodiments means that the isolated protein is substantially free of cellular material and includes preparations of protein having less than about 30%, 20%, 10%, or 5% (by dry weight) of contaminating protein. When the protein of the embodiments or biologically active portion thereof is recombinantly produced, culture medium represents less than about 30%, 20%, 10%, or 5% (by dry weight) of chemical precursors or non-protein-of-interest chemicals.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

As used herein, the term "impacting insect pests" refers to effecting changes in insect feeding, growth, and/or behavior at any stage of development, including but not limited to: killing the insect; retarding growth; preventing reproductive capability; antifeedant activity; and the like.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. For example, "pesticidal proteins" are proteins that display pesticidal activity by themselves or in combination with other proteins.

As used herein, the term "pesticidally effective amount" means a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest.

As used herein, the term "recombinantly engineered" or "engineered" means the utilization of recombinant DNA technology to introduce (e.g., engineer) a change in the protein structure based on an understanding of the protein's mechanism of action and a consideration of the amino acids being introduced, deleted, or substituted.

As used herein, the term "mutant nucleotide sequence" or "mutation" or "mutagenized nucleotide sequence" means a nucleotide sequence that has been mutagenized or altered to contain one or more nucleotide residues (e.g., base pair) that is not present in the corresponding wild-type sequence. Such mutagenesis or alteration consists of one or more additions, deletions, or substitutions or replacements of nucleic acid residues. When mutations are made by adding, removing, or replacing an amino acid of a proteolytic site, such addition, removal, or replacement may be within or adjacent to the proteolytic site motif, so long as the object of the mutation is accomplished (i.e., so long as proteolysis at the site is changed).

A mutant nucleotide sequence can encode a variant insecticidal toxin showing improved or decreased insecticidal activity, or an amino acid sequence which confers improved or decreased insecticidal activity on a polypeptide containing it. As used herein, the term "variant" or "mutation" in the context of a protein a polypeptide or amino acid sequence refers to a sequence which has been mutagenized or altered to contain one or more amino acid residues that are not present in the corresponding wild-type sequence. Such mutagenesis or alteration consists of one or more additions, deletions, or substitutions or replacements of amino acid residues. A variant polypeptide shows improved or decreased insecticidal activity, or represents an amino acid sequence which confers improved insecticidal activity on a polypeptide containing it. Thus, the term "variant" or "mutation" refers to either or both of the mutant nucleotide sequence and the encoded amino acids. Variants may be used alone or in any compatible combination with other variants of the embodiments or with other pesticidal polypeptides. A variant polypeptide may conversely show a decrease in insecticidal activity. Where more than one mutation is added to a particular nucleic acid or protein, the mutations may be added at the same time or sequentially; if sequentially, mutations may be added in any suitable order.

As used herein, the term "improved insecticidal activity" or "improved pesticidal activity" refers to an insecticidal polypeptide of the embodiments that has enhanced insecticidal activity relative to the activity of its corresponding wild-type protein, and/or an insecticidal polypeptide that is effective against a broader range of insects, and/or an insecticidal polypeptide having specificity for an insect that is not susceptible to the toxicity of the wild-type protein. A finding of improved or enhanced pesticidal activity requires a demonstration of an increase of pesticidal activity of at least 10%, against the insect target, or at least 20%, 25%, 30%, 35%, 40%, 45%, 50%, 60%, 70%, 100%, 150%, 200%, or 300% or greater increase of pesticidal activity relative to the pesticidal activity of the wild-type insecticidal polypeptide determined against the same insect.

For example, an improved pesticidal or insecticidal activity is provided where a wider or narrower range of insects is impacted by the polypeptide relative to the range of insects that is affected by a wild-type Bt toxin. A wider range of impact may be desirable where versatility is desired, while a narrower range of impact may be desirable where, for example, beneficial insects might otherwise be impacted by use or presence of the toxin. While the embodiments are not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

The term "toxin" as used herein refers to a polypeptide showing pesticidal activity or insecticidal activity or improved pesticidal activity or improved insecticidal activity. "Bt" or "*Bacillus thuringiensis*" toxin is intended to include the broader class of Cry toxins found in various strains of Bt, which includes such toxins as, for example, Cry1s, Cry2s, or Cry3s.

The terms "proteolytic site" or "cleavage site" refer to an amino acid sequence which confers sensitivity to a class of proteases or a particular protease such that a polypeptide containing the amino acid sequence is digested by the class of proteases or particular protease. A proteolytic site is said to be "sensitive" to the protease(s) that recognize that site. It is appreciated in the art that the efficiency of digestion will vary, and that a decrease in efficiency of digestion can lead to an increase in stability or longevity of the polypeptide in an insect gut. Thus, a proteolytic site may confer sensitivity to more than one protease or class of proteases, but the efficiency of digestion at that site by various proteases may vary. Proteolytic sites include, for example, trypsin sites, chymotrypsin sites, and elastase sites.

The variant polypeptides of the embodiments are generally prepared by a process that involves the steps of: obtaining a nucleic acid sequence encoding a Cry family polypeptide; analyzing the structure of the polypeptide to identify particular "target" sites for mutagenesis of the underlying gene sequence based on a consideration of the proposed function of the target domain in the mode of action of the toxin; introducing one or more mutations into the nucleic acid sequence to produce a desired change in one or more amino acid residues of the encoded polypeptide sequence; and assaying the polypeptide produced for pesticidal activity.

Under sporulation conditions, *Bacillus thuringiensis* (Bt) produces insecticidal proteins, named Cry or Cyt that are toxic to different insect orders (Pardo-López et al., *FEMS Microbiology Reviews* 37, 3-22 2013). Bt toxins have been commercially used to control important insect agricultural pests and also in controlling dipteran vectors of human diseases (Sanahuja et al., *Plant Biotecnol J* 9, 283-3002011).

Cry toxins of the three-domain family show a similar fold composed of three domains where domain I is a seven α-helix bundle and domains II and II are mostly composed of β-sheets. The three domain Cry family of proteins and have members with insecticidal activity against different insect orders (Pardo-López et al., *FEMS Microbiology Reviews* 37, 3-22 2013).

In contrast Cyt toxins are composed of a single α-β domain with seven to eight β-strands wrapped by α-helices (Bravo et al, *Insect Biochem. Mol. Biol.* 41: 423-431 2011; Soberon et al., *Peptides.* 41: 87-93 2013). Cyt toxins are mostly active against dipteran larvae and they are found principally in Bt strains that are active against dipteran along with different mosquitocidal three domain Cry toxins. It was also shown that Cyt1Aa show toxicity against certain coleopteran pest, *Chrysomela scripta* (Federeci and Bauer, *Appl. Environ. Microbiol.*, 64, 4368-4371 1998). In addition, Cyt toxins have cytolytic activity against a broad range of mammalian cultured cells and also to red blood cells (Knowles et al., *Proc. R. Soc. Lon.* 248, 1-7 1992). In contrast to three domain Cry toxins that rely in the specific binding to larvae midgut proteins to form oligomers and form pores (Bravo et al, *Insect Biochem. Mol. Biol.* 41: 423-431 2011), Cyt toxins form high molecular weight oligomers that insert into the membrane forming lytic pores (Rodriguez-Almazan et al., *Biochemistry* 50: 388-396 2011; López-Diaz et al., *Environm Microbiol.* 15: 330-3039 2013). Direct binding to membrane lipids explains their unspecific cytolytic activity. It has been proposed that β5-β7 region is likely involved in Cyt1Aa membrane insertion while α-A and α-C helices are involved in Cyt1Aa oligomerization (Cohen et al., *Mol Biol* 413: 804-814 2011; Lopez-Diaz et al., *Environm Microbiol.* 15: 330-3039 2013).

One of the most interesting features of Cyt1Aa is its capacity to synergize the toxicity of different three domain Cry toxins such as Cry11Aa and Cry4Ba (Crickmore et al., *EMS Microbiol Lett* 131: 249-254 1995; Canton et al., *Peptides.* 53: 286-291 2011; Perez et al., *Proc Natl Acad Sci USA* 102: 18303-18308 2005). Moreover Cyt1Aa overcomes resistance of *Culex quinquefasciatus* to Cry4Ba or Cry11Aa (Wirth et al., *Proc Natl Acad Sci USA* 9: 10536-10540 1997). It has been proposed that Cyt1Aa is a functional receptor of Cry11Aa since binding of this toxin to Cyt1Aa facilitates oligomer formation and membrane insertion (Pérez et al., *Proc Natl Acad Sci USA* 102: 18303-18308 2005; Pérez et al., *Cell Microbiol* 9: 2931-2937 2007).

It has been shown that oligomerization of Cyt1Aa is a key step in membrane binding and pore formation (López-Diaz et al., *Environm Microbiol.* 15: 330-3039 2013). Cyt1Aa mutations in helix α-C residues showed that certain mutations that affected oligomerization and membrane insertion were not toxic to *Aedes aegypti* larvae and also lost their hemolytic activity indicating that oligomerization is a key step in Cty1Aa toxicity (López-Diaz et al., *Environm Microbiol.* 15: 330-3039 2013). By making use of synthetic peptides corresponding to the different secondary structures of Cyt1Aa, it was shown that α-A and α-C helices are major structural regions involved in initial membrane binding and toxin oligomerization (Gazit and Shai, Biochemistry 32, 12363-12371 1993; Gazit et al., *Biochemistry* 36, 15546-15554 1997). In the case of Cyt2Aa, mutations of certain amino acid residues in helices α-A and α-C also showed a similar phenotype since variants affected in oligomerization affected insecticidal and hemolytic activities of the protein (Promdonkoy et al., *J. Biotechnol.* 133, 287-293 2008).

To determine the role of Cyt1Aa helix α-A in the mode of action of this toxin, several residues of this region were mutated and the variants analyzed for oligomerization, synergism of Cry11Aa, as well as in insecticidal and hemolytic activities. Interestingly our results show that two variants located in helix α-A were affected in hemolysis of red blood cells, but were not affected in oligomerization and synergism to Cry11Aa, retaining significant toxicity against *A. aegypti* larvae. These results show that helix α-A from Cyt1Aa has a differential role in the insecticidal and hemolytic activities of the toxin.

It will be appreciated by those of skill in the art that any useful mutation may be added to the sequences of the embodiments so long as the encoded polypeptides retain pesticidal activity. Thus, sequences may also be mutated so that the encoded polypeptides are resistant to proteolytic digestion by chymotrypsin. More than one recognition site can be added in a particular location in any combination, and multiple recognition sites can be added to or removed from the toxin. Thus, additional mutations can comprise three, four, or more recognition sites. It is to be recognized that multiple mutations can be engineered in any suitable polynucleotide sequence; accordingly, either full-length sequences or fragments thereof can be modified to contain additional or alternative cleavage sites as well as to be resistant to proteolytic digestion. In this manner, the embodiments provide Cry toxins containing mutations that improve pesticidal activity as well as improved compositions and methods for impacting pests using other Bt toxins.

Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a variant polypeptide with wild-type toxins or by comparing variant toxins which differ in their amino acid sequence. Putative proteolytic sites and proteolytic sites include, but are not limited to, the following sequences: RR, a trypsin cleavage site; LKM, a chymotrypsin site; and a trypsin site. These sites may be altered by the addition or deletion of any number and kind of amino acid residues, so long as the pesticidal activity of the polypeptide is increased. Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

Compositions of the embodiments include nucleic acids, and fragments and variants thereof that encode Cyt1A variant polypeptides. In particular, the embodiments provide for isolated nucleic acid molecules comprising nucleotide sequences encoding the amino acid sequence shown in SEQ ID NO: 4 and SEQ ID NO: 6, or the nucleotide sequences encoding said amino acid sequence, for example the nucleotide sequence set forth in SEQ ID NO: 3 and SEQ ID NO: 5, and fragments and variants thereof.

Also of interest are optimized nucleotide sequences encoding the Cyt1A variant polypeptides of the embodiments. As used herein, the phrase "optimized nucleotide sequences" refers to nucleic acids that are optimized for expression in a particular organism, for example a plant. Optimized nucleotide sequences may be prepared for any organism of interest using methods known in the art. See, for example, U.S. Pat. No. 7,462,760, which describes an optimized nucleotide sequence encoding a disclosed pesticidal protein. In this example, the nucleotide sequence was prepared by reverse-translating the amino acid sequence of the protein and changing the nucleotide sequence so as to comprise maize-preferred codons while still encoding the same amino acid sequence. This procedure is described in more detail by Murray et al. (1989) *Nucleic Acids Res.* 17:477-498. Optimized nucleotide sequences find use in increasing expression of a Cyt1A variant polypeptide in a plant, for example monocot plants of the Gramineae (Poaceae) family such as, for example, a maize or corn plant.

In some embodiments the nucleic acid molecule encoding the polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

The embodiments further provide isolated pesticidal (e.g., insecticidal) polypeptides encoded by either a naturally-occurring or modified nucleic acid of the embodiments. More specifically, the embodiments provide polypeptides comprising an amino acid sequence set forth in SEQ ID NO: 4 and SEQ ID NO: 6, and the polypeptides encoded by nucleic acids described herein, for example those set forth in SEQ ID NO: 3 and SEQ ID NO: 5, and fragments and variants thereof.

In particular embodiments, Cyt1A variant polypeptides of the embodiments provide full-length insecticidal polypeptides, fragments of full-length insecticidal polypeptides, and variant polypeptides that are produced from mutagenized nucleic acids designed to introduce particular amino acid sequences into polypeptides of the embodiments. In particular embodiments, the amino acid sequences that are introduced into the polypeptides comprise a sequence that provides a cleavage site for an enzyme such as a protease.

It is known in the art that the pesticidal activity of Bt toxins is typically activated by cleavage of the peptide in the insect gut by various proteases. Because peptides may not always be cleaved with complete efficiency in the insect gut, fragments of a full-length toxin may have enhanced pesticidal activity in comparison to the full-length toxin itself. Thus, some of the polypeptides of the embodiments include fragments of a full-length insecticidal polypeptide, and some of the polypeptide fragments, variants, and mutations will have enhanced pesticidal activity relative to the activity of the naturally occurring insecticidal polypeptide from which they are derived, particularly if the naturally occurring insecticidal polypeptide is not activated in vitro with a protease prior to screening for activity. Thus, the present application encompasses truncated versions or fragments of the sequences.

Mutations may be placed into any background sequence, including such truncated polypeptides, so long as the polypeptide retains pesticidal activity. One of skill in the art can readily compare two or more proteins with regard to pesticidal activity using assays known in the art or described elsewhere herein. It is to be understood that the polypeptides of the embodiments can be produced either by expression of a nucleic acid disclosed herein, or by the use of standard molecular biology techniques.

It is recognized that the Cyt1A variant polypeptides may be oligomeric and will vary in molecular weight, number of residues, component peptides, activity against particular pests, and other characteristics. However, by the methods set forth herein, proteins active against a variety of pests may be isolated and characterized. The Cyt1A variant polypeptides of the embodiments can be used in combination with other Bt toxins or other insecticidal proteins to increase insect target range. Furthermore, the use of the Cyt1A variant polypeptides of the embodiments in combination with other Bt toxins or other insecticidal principles of a distinct nature has particular utility for the prevention and/or management of insect resistance. Other insecticidal agents include protease inhibitors (both serine and cysteine types), α-amylase, and peroxidase.

Fragments and variants of the nucleotide and amino acid sequences and the polypeptides encoded thereby are also encompassed by the embodiments. As used herein the term "fragment" refers to a portion of a nucleotide sequence of a polynucleotide or a portion of an amino acid sequence of a polypeptide of the embodiments. Fragments of a nucleotide sequence may encode protein fragments that retain the biological activity of the native or corresponding full-length protein and hence possess pesticidal activity. Thus, it is acknowledged that some of the polynucleotide and amino acid sequences of the embodiments can correctly be referred to as both fragments and variants.

It is to be understood that the term "fragment," as it is used to refer to nucleic acid sequences of the embodiments, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the embodiments.

A fragment of a nucleotide sequence of the embodiments that encodes a biologically active portion of a Cyt1A variant polypeptide of the embodiments will encode at least 15, 25, 30, 50, 100, 150, 175, 200 or 225 contiguous amino acids, or up to the total number of amino acids present in a pesticidal polypeptide of the embodiments (for example, 249 amino acids for SEQ ID NO: 4 or SEQ ID NO: 6). Thus, it is understood that the embodiments also encompass polypeptides that are fragments of the exemplary Cyt1A variant polypeptides of the embodiments and having lengths of at least 15, 25, 30, 50, 100, 150, 175, 200 or 225 contiguous amino acids, or up to the total number of amino acids present in a pesticidal polypeptide of the embodiments (for example, 249 amino acids for SEQ ID NO: 4 or SEQ ID NO: 6). Fragments of a nucleotide sequence of the embodiments that are useful as hybridization probes or PCR primers generally need not encode a biologically active portion of a Cyt1A variant polypeptide. Thus, a fragment of a nucleic acid of the embodiments may encode a biologically active portion of a Cyt1A variant polypeptide, or it may be a fragment that can be used as a hybridization probe or PCR primer using methods disclosed herein. A biologically active portion of a Cyt1A variant polypeptide can be prepared by isolating a portion of one of the nucleotide sequences of the embodiments, expressing the encoded portion of the Cyt1A variant polypeptide (e.g., by recombinant expression in vitro), and assessing the activity of the encoded portion of the Cyt1A variant polypeptide.

Nucleic acids that are fragments of a nucleotide sequence of the embodiments comprise at least 16, 20, 50, 75, 100, 150, 200, 250, 300, 350, 400, 450, 500, 600 or 700, nucleotides, or up to the number of nucleotides present in a nucleotide sequence disclosed herein (for example, 747 nucleotides for SEQ ID NO: 3 or SEQ ID NO: 5). Particular embodiments envision fragments derived from (e.g., produced from) a first nucleic acid of the embodiments, wherein the fragment encodes a truncated toxin characterized by pesticidal activity. Truncated polypeptides encoded by the polynucleotide fragments of the embodiments are characterized by pesticidal activity that is either equivalent to, or improved, relative to the activity of the corresponding full-length polypeptide encoded by the first nucleic acid from which the fragment is derived. It is envisioned that such nucleic acid fragments of the embodiments may be truncated at the 3' end of the native or corresponding full-length coding sequence. Nucleic acid fragments may also be truncated at both the 5' and 3' end of the native or corresponding full-length coding sequence.

The term "variants" is used herein to include substantially similar sequences. For nucleotide sequences, conservative variants include those sequences that, because of the degeneracy of the genetic code, encode the amino acid sequence of one of the pesticidal polypeptides of the embodiments. Those having ordinary skill in the art will readily appreciate that due to the degeneracy of the genetic code, a multitude of nucleotide sequences encoding of the present invention exist. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gown, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. See, for example, U.S. Pat. Nos. 5,380,831, and 5,436,391 and Murray, et al., (1989) *Nucleic Acids Res.* 17:477-498, and Liu H et al. *Mol Bio Rep* 37:677-684, 2010, herein incorporated by reference. A *Zea* maize codon usage table can be also found at kazusa.or.jp/codon/cgi-bin/showcodon.cgi?species=4577, which can be accessed using the www prefix.

A *Glycine max* codon usage table can be found at kazusa.or.jp/codon/cgi-bin/showcodon.cgi?species=3847&aa=1&style=N, which can be accessed using the www prefix.

The skilled artisan will further appreciate that changes can be introduced by mutation of the nucleic acid sequences thereby leading to changes in the amino acid sequence of the encoded polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present invention.

Naturally occurring allelic variants such as these can be identified with the use of well-known molecular biology techniques, such as, for example, polymerase chain reaction (PCR) and hybridization techniques as outlined herein.

Variant nucleotide sequences also include synthetically derived nucleotide sequences, such as those generated, for example, by using site-directed mutagenesis but which still encode a Cyt1A variant polypeptide of the embodiments, such as a variant toxin. Generally, variants of a particular nucleotide sequence of the embodiments will have at least about 70%, 75%, 80%, 85%, 86%, 87%, 88%, 89%, 90%, 91%, 92%, 93%, 94%, 95%, 96%, 97%, 98%, 99%, or more sequence identity to that particular nucleotide sequence as determined by sequence alignment programs described elsewhere herein using default parameters. A variant of a nucleotide sequence of the embodiments may differ from that sequence by as few as 1-15 nucleotides, as few as 1-10, such as 6-10, as few as 5, as few as 4, 3, 2, or even 1 nucleotide.

Variants of a particular nucleotide sequence of the embodiments (i.e., an exemplary nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptide of SEQ ID NO: 4 or SEQ ID NO: 6 are disclosed. Percent sequence identity between any two polypeptides can be calculated using sequence alignment programs described elsewhere herein using default parameters. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

As used herein, the term "variant protein" encompasses polypeptides that are derived from a native protein by: deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Accordingly, the term "variant protein" encompasses biologically active fragments of a native protein that comprise a sufficient number of contiguous amino acid residues to retain the biological activity of the native protein, i.e., to have pesticidal activity. Such pesticidal activity may be different or improved relative to the native protein or it may be unchanged, so long as pesticidal activity is retained.

Variant proteins encompassed by the embodiments are biologically active, that is they continue to possess the desired biological activity of the native protein, that is, pesticidal activity as described herein. Such variants may result from, for example, genetic polymorphism or from human manipulation. Biologically active Cyt1A variant polypeptides of a native pesticidal protein of the embodiments will have at least about 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence as determined by sequence alignment programs described elsewhere herein using default parameters. A biologically active variant of a protein of the embodiments may differ from that protein by as few as 1-15 amino acid residues, as few as 1-10, such as 6-10, as few as 5, as few as 4, 3, 2, or even 1 amino acid residue.

In some embodiments the Cyt1A variant polypeptide comprising an amino acid sequence having an amino acid substitution at a residue corresponding to position 59 or 61 of SEQ ID NO: 2 and the Cyt1A variant polypeptide has decreased hemolytic activity compared to the Cyt1A polypeptide of SEQ ID NO: 2.

In some embodiments the Cyt1A variant polypeptide comprising an amino acid sequence having a cysteine amino acid substitution at a residue corresponding to position 59 or 61 of SEQ ID NO: 2 and the Cyt1A variant polypeptide has decreased hemolytic activity compared to the Cyt1A polypeptide of SEQ ID NO: 2.

In some embodiments the Cyt1A variant polypeptide comprising an amino acid sequence having at least 95% sequence identity to SEQ ID NO: 2, an amino acid substitution at position 59 or 61 of SEQ ID NO: 2, and decreased hemolytic activity compared to the Cyt1A polypeptide of SEQ ID NO: 2.

In some embodiments the Cyt1A variant polypeptide comprising an amino acid sequence having at least 95% sequence identity to SEQ ID NO: 2, a cysteine amino acid substitution at position 59 or 61 of SEQ ID NO: 2, and decreased hemolytic activity compared to the Cyt1A polypeptide of SEQ ID NO: 2.

In some embodiments the Cyt1A variant polypeptide has at least 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence of SEQ ID NO: 4 or SEQ ID NO: 6.

In some embodiments the Cyt1A variant polypeptide has at least 95%, sequence identity to the amino acid sequence of SEQ ID NO: 4 or SEQ ID NO: 6.

In some embodiments the Cyt1A variant polypeptide comprises the amino acid sequence of SEQ ID NO: 4 or SEQ ID NO: 6.

In some embodiments the Cyt1A variant polypeptide consists essentially of the amino acid sequence of SEQ ID NO: 4 or SEQ ID NO: 6.

In some embodiments the Cyt1A variant polypeptide consists of the amino acid sequence of SEQ ID NO: 4 or SEQ ID NO: 6.

In some embodiments the polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments the polypeptide has increased digestibility of proteolytic fragments in an insect gut. In some embodiments the polypeptide has increased stability in an insect gut. Models for digestion by simulated simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al J. Agric Food Chem. 50: 7154-7160, 2002). In some embodiments the Cyt1A variant polypeptide has decreased hemolytic activity compared Cyt1Aa (SEQ ID NO: 2).

The embodiments further encompass a microorganism that is transformed with at least one nucleic acid of the embodiments, with an expression cassette comprising the nucleic acid, or with a vector comprising the expression cassette. In some embodiments, the microorganism is one that multiplies on plants. An embodiment of the invention relates to an encapsulated Cyt1A variant polypeptide which comprises a transformed microorganism capable of expressing at least one Cyt1A variant polypeptide of the embodiments.

The embodiments provide pesticidal compositions comprising a transformed microorganism of the embodiments. In such embodiments, the transformed microorganism is generally present in the pesticidal composition in a pesticidally effective amount, together with a suitable carrier. The embodiments also encompass pesticidal compositions comprising an isolated protein of the embodiments, alone or in combination with a transformed organism of the embodiments and/or an encapsulated Cyt1A variant polypeptide of the embodiments, in an insecticidally effective amount, together with a suitable carrier.

The embodiments further provide a method of increasing insect target range by using a Cyt1A variant polypeptide of the embodiments in combination with at least one other or "second" pesticidal protein. Any pesticidal protein known in the art can be employed in the methods of the embodiments. Such pesticidal proteins include, but are not limited to, Bt toxins, protease inhibitors, α-amylases, and peroxidases.

The embodiments also encompass transformed or transgenic plants comprising at least one nucleotide sequence of the embodiments. In some embodiments, the plant is stably transformed with a nucleotide construct comprising at least one nucleotide sequence of the embodiments operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes whole plants, plant organs (e.g., leaves, stems, roots, etc.), seeds, plant cells, and progeny of same. Parts of transgenic plants are within the scope of the embodiments and comprise, for example, plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, originating in transgenic plants or their progeny previously transformed with a DNA molecule of the embodiments and therefore consisting at least in part of transgenic cells. The class of plants that can be used in the methods of the embodiments is generally as broad as the class of higher plants amenable to transformation techniques, including both monocotyledonous and dicotyledonous plants.

While the embodiments do not depend on a particular biological mechanism for increasing the resistance of a plant to a plant pest, expression of the nucleotide sequences of the embodiments in a plant can result in the production of the Cyt1A variant polypeptides of the embodiments and in an increase in the resistance of the plant to a plant pest. The plants of the embodiments find use in agriculture in methods for impacting insect pests. Certain embodiments provide transformed crop plants, such as, for example, maize plants, which find use in methods for impacting insect pests of the plant, such as, for example, Lepidopteran pests.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

One of skill in the art will readily acknowledge that advances in the field of molecular biology such as site-specific and random mutagenesis, polymerase chain reaction methodologies, and protein engineering techniques provide an extensive collection of tools and protocols suitable for use to alter or engineer both the amino acid sequence and underlying genetic sequences of proteins of agricultural interest.

Thus, the proteins of the embodiments may be altered in various ways including amino acid substitutions, deletions, truncations, and insertions. Methods for such manipulations are generally known in the art. For example, amino acid sequence variants of the Cyt1A variant polypeptides can be prepared by introducing mutations into a synthetic nucleic acid (e.g., DNA molecule). Methods for mutagenesis and nucleic acid alterations are well known in the art. For example, designed changes can be introduced using an oligonucleotide-mediated site-directed mutagenesis technique. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York), and the references cited therein.

The mutagenized nucleotide sequences of the embodiments may be modified so as to change about 1, 2, 3, 4, 5, 6, 8, 10, 12 or more of the amino acids present in the primary sequence of the encoded polypeptide. Alternatively, even more changes from the native sequence may be introduced such that the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more of the codons altered, or otherwise modified compared to the corresponding wild-type protein. In the same manner, the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more additional codons compared to the corresponding wild-type protein. It should be understood that the mutagenized nucleotide sequences of the embodiments are intended to encompass biologically functional, equivalent peptides which have pesticidal activity, such as an improved pesticidal activity as determined by antifeedant properties against European corn borer larvae. Such sequences may arise as a consequence of codon redundancy and functional equivalency that are known to occur naturally within nucleic acid sequences and the proteins thus encoded.

One of skill in the art would recognize that amino acid additions and/or substitutions are generally based on the relative similarity of the amino acid side-chain substituents, for example, their hydrophobicity, charge, size, and the like. Exemplary amino acid substitution groups that take various of the foregoing characteristics into consideration are well known to those of skill in the art and include: arginine and lysine; glutamate and aspartate; serine and threonine; glutamine and asparagine; and valine, leucine, and isoleucine.

Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the embodiments include both the naturally occurring sequences and variant forms. Likewise, the proteins of the embodiments encompass both naturally occurring proteins and variations (e.g., truncated polypeptides) and modified (e.g., variant) forms thereof. Such variants will continue to possess the desired pesticidal activity. Obviously, the mutations that will be made in the nucleotide sequence encoding the variant must not place the sequence out of reading frame and generally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, such as insect-feeding assays. See, for example, Marrone et al. (1985) *J. Econ. Entomol.* 78: 290-293 and Czapla and Lang (1990) *J. Econ. Entomol.* 83: 2480-2485, herein incorporated by reference.

Variant nucleotide sequences and proteins also encompass sequences and proteins derived from a mutagenic and recombinogenic procedure such as DNA shuffling. With such a procedure, one or more different coding sequences can be manipulated to create a new Cyt1A variant polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequence of the embodiments may be shuffled between the nucleotide sequences of the embodiments and corresponding portions of other known Cyt1A nucleotide sequences to obtain a new gene coding for a protein with an improved property of interest.

Properties of interest include, but are not limited to, pesticidal activity per unit of Cyt1A variant polypeptide, protein stability, and toxicity to non-target species particularly humans, livestock, and plants and microbes that express the pesticidal polypeptides of the embodiments. The embodiments are not bound by a particular shuffling strategy, only that at least one nucleotide sequence of the embodiments, or part thereof, is involved in such a shuffling strategy. Shuffling may involve only nucleotide sequences disclosed herein or may additionally involve shuffling of other nucleotide sequences known in the art. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the embodiments can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter "Sambrook". See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art and are disclosed in Sambrook.

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding Cyt1A sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Using standard equations, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration can be increased so that a higher temperature can be used. An extensive guide to the hybridization of nucleic acids is found in Tijssen (1993) *Laboratory Techniques in Biochemistry and Molecular Biology Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See also Sambrook. Thus, isolated sequences that encode a Cyt1A protein of the embodiments and hybridize under stringent conditions to the Cry sequences disclosed herein, or to fragments thereof, are encompassed by the embodiments.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994)*Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST® programs of Altschul et al (1990) *J. Mol. Biol.* 215:403 are based on the algorithm of Karlin and Altschul (1990) supra. BLAST® nucleotide searches can be performed with the BLASTN® program, score=100, wordlength=12, to obtain nucleotide sequences homologous to a nucleotide sequence encoding a protein of the embodiments. protein searches can be performed with the BLASTX® program, score=50, wordlength=3, to obtain amino acid sequences homologous to a protein or polypeptide of the embodiments. To obtain gapped alignments for comparison purposes, Gapped BLAST® (in BLAST® 2.0) can be utilized as described in Altschul et al. (1997) *Nucleic Acids Res.* 25:3389. Alternatively, PSI-BLAST® (in BLAST® 2.0) can be used to perform an iterated search that detects distant relationships between molecules. See Altschul et al. (1997) supra. When utilizing BLAST®, Gapped BLAST®, PSI-BLAST®, the default parameters of the respective programs (e.g., BLASTN® for nucleotide sequences, BLASTX® for proteins) can be used. See the National Center for Biotechnology Information website on the world wide web at ncbi.hlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. The term "equivalent program" as used herein refers to any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures, and the like.

A further embodiment relates to a transformed organism such as an organism selected from the group consisting of plant and insect cells, bacteria, yeast, baculoviruses, protozoa, nematodes, and algae. The transformed organism comprises: a DNA molecule of the embodiments, an expression cassette comprising the said DNA molecule, or a vector comprising the said expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous, and, where necessary to join two protein coding regions, contiguous and in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the Cyt1A toxin sequence to be under the transcriptional regulation of the regulatory regions. The DNA construct may additionally contain selectable marker genes.

The DNA construct will include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

The termination region may be native with the transcriptional initiation region, may be native with the operably linked DNA sequence of interest, may be native with the plant host, or may be derived from another source (i.e., foreign or heterologous to the promoter, the sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray et al., supra. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli*, or eukaryotic cells such as yeast, insect, amphibian, or mammalian cells, or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus), human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245-254; Uknes et al. (1992) *Plant Cell* 4: 645-656; and Van Loon (1985) *Plant Mol. Virol.* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced Cyt1A variant polypeptide expression within a particular plant tissue. Tissue-preferred promoters include those discussed in Yamamoto et al. (1997) *Plant J.* 12(2) 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a (3-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teen et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene fused to nptll (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Ciml (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glob-1 are endosperm-specific promoters. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference. A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; and Meijer et al. (1991) *Plant Mol. Biol.* 16:807-820); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481; and U.S. Pat. Nos. 7,709,702; and 7,462,481); phosphinothricin (DeBlock et al. (1987) *EMBO J.* 6:2513-2518). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Sci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); and Gill et al. (1988) *Nature* 334: 721-724. Such disclosures are herein incorporated by reference.

The above list of selectable marker genes is not meant to be limiting. Any selectable marker gene can be used in the embodiments.

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606), *Agrobacterium*-mediated transformation (U.S. Pat. Nos. 5,563,055 and 5,981,840), direct gene transfer (Paszkowski et al. (1984) *EMBO J.* 3: 2717-2722), and ballistic particle acceleration (see, for example, U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6: 923-926); and Lec1 transformation (WO 00/28058). For potato transformation see Tu et al. (1998) *Plant Molecular Biology* 37: 829-838 and Chong et al. (2000) *Transgenic Research* 9: 71-78. Additional transformation procedures can be found in Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91: 440-444 (maize); Fromm et al. (1990) *Biotechnology* 8: 833-839 (maize); Hooykaas-Van Slogteren et al. (1984) *Nature* (London) 311: 763-764; U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation);

D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the Cyt1A toxin protein or variants and fragments thereof directly into the plant or the introduction of the Cyt1A toxin transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the Cyt1A variant polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma # P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired Cyt1A variant polypeptide. It is also recognized that such a viral polyprotein, comprising at least a portion of the amino acid sequence of a Cyt1A variant polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367; and 5,316,931; herein incorporated by reference.

The embodiments further relate to plant-propagating material of a transformed plant of the embodiments including, but not limited to, seeds, tubers, corms, bulbs, leaves, and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tuhpa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants, including, but not limited to: corn, alfalfa, sunflower, *Brassica* spp., soybean, cotton, safflower, peanut, sorghum, wheat, millet, tobacco, sugarcane, etc.

Turfgrasses include, but are not limited to: annual bluegrass (*Poa annua*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropy-* ron desertorum); fairway wheatgrass (Agropyron cristatum); hard fescue (Festuca longifolia); Kentucky bluegrass (Poa pratensis); orchardgrass (Dactylis glomerata); perennial ryegrass (Lolium perenne); red fescue (Festuca rubra); redtop (Agrostis alba); rough bluegrass (Poa trivialis); sheep fescue (Festuca ovina); smooth bromegrass (Bromus inermis); tall fescue (Festuca arundinacea); timothy (Phleum pratense); velvet bentgrass (Agrostis canina); weeping alkaligrass (Puccinellia distans); western wheatgrass (Agropyron smithii); Bermuda grass (Cynodon spp.); St. Augustine grass (Stenotaphrum secundatum); zoysia grass (Zoysia spp.); Bahia grass (Paspalum notatum); carpet grass (Axonopus affinis); centipede grass (Eremochloa ophiuroides); kikuyu grass (Pennisetum clandesinum); seashore paspalum (Paspalum vaginatum); blue gramma (Bouteloua gracilis); buffalo grass (Buchloe dactyloids); sideoats gramma (Bouteloua curtipendula).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, Brassica, maize, alfalfa, palm, coconut, flax, castor, olive etc. Leguminous plants include beans and peas. Beans include guar, locust bean, fenugreek, soybean, garden beans, cowpea, mung bean, lima bean, fava bean, lentils, chickpea, etc.

In certain embodiments the nucleic acid sequences of the embodiments can be stacked with any combination of polynucleotide sequences of interest in order to create plants with a desired phenotype. For example, the polynucleotides of the embodiments may be stacked with any other polynucleotides encoding polypeptides having pesticidal and/or insecticidal activity, such as other Bt toxic proteins (described in U.S. Pat. Nos. 5,366,892; 5,747,450; 5,736,514; 5,723,756; 5,593,881; and Geiser et al. (1986) Gene 48:109), pentin (described in U.S. Pat. No. 5,981,722) and the like. The combinations generated can also include multiple copies of any one of the polynucleotides of interest. The polynucleotides of the embodiments can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,049); barley high lysine (Williamson et al. (1987) Eur. J. Biochem. 165: 99-106; and WO 98/20122) and high methionine proteins (Pedersen et al. (1986) J. Biol. Chem. 261: 6279; Kirihara et al. (1988) Gene 71: 359; and Musumura et al. (1989) Plant Mol. Biol. 12: 123)); increased digestibility (e.g., modified storage proteins (U.S. Pat. No. 6,858,778); and thioredoxins (U.S. Pat. No. 7,009,087), the disclosures of which are herein incorporated by reference.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al. (1994) Science 266:789; Martin et al. (1993) Science 262: 1432; and Mindrinos et al. (1994) Cell 78:1089); acetolactate synthase (ALS) variants that lead to herbicide resistance such as the S4 and/or Hra mutations; inhibitors of glutamine synthase such as phosphinothricin or basta (e.g., bar gene); and glyphosate resistance (EPSPS gene and GAT gene as disclosed in U.S. Pat. Nos. 7,709,702; and 7,462,481; and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170: 5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

In some embodiment the stacked trait may be a trait or event that has received regulatory approval including but not limited to the events well known to one skilled in the art which can be found at the Center for Environmental Risk Assessment (cera-gmc.org/?action=gm_crop_database, which can be accessed using the www prefix) and at the International Service for the Acquisition of Agri-Biotech Applications isaaa.org/gmapprovaldatabase/default.asp, which can be accessed using the www prefix).

These stacked combinations can be created by any method including but not limited to cross breeding plants by any conventional or TOPCROSS® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Compositions of the embodiments find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the embodiments comprising a nucleotide sequence encoding a Cyt1A variant polypeptide of the embodiments may be treated with a seed protectant coating comprising a seed treatment compound, such as, for example, captan, carboxin, thiram, methalaxyl, pirimiphosmethyl, and others that are commonly used in seed treatment. In one embodiment, a seed protectant coating comprising a pesticidal composition of the embodiments is used alone or in combination with one of the seed protectant coatings customarily used in seed treatment.

It is recognized that the genes encoding the Cyt1A variant polypeptides can be used to transform insect pathogenic organisms. Such organisms include baculoviruses, fungi, protozoa, bacteria, and nematodes.

A gene encoding a Cyt1A variant polypeptide of the embodiments may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the Cyt1A variant polypeptide, and desirably, provide for improved protection of the pesticide from environmental degradation and inactivation.

Such microorganisms include bacteria, algae, and fungi. Of particular interest are microorganisms such as bacteria, e.g., *Pseudomonas*, *Erwinia*, *Serratia*, *Klebsiella*, *Xanthomonas*, *Streptomyces*, *Rhizobium*, *Rhodopseudomonas*, *Methylius*, *Agrobacterium*, *Acetobacter*, *Lactobacillus*, *Arthrobacter*, *Azotobacter*, *Leuconostoc*, and *Alcaligenes*, fungi, particularly yeast, e.g., *Saccharomyces*, *Cryptococcus*, *Kluyveromyces*, *Sporobolomyces*, *Rhodotorula*, and *Aureobasidium*. Of particular interest are such phytosphere bacterial species as *Pseudomonas syringae*, *Pseudomonas fluorescens*, *Serratia marcescens*, *Acetobacter xylinum*, *Agrobacteria*, *Rhodopseudomonas spheroides*, *Xanthomonas campestris*, *Rhizobium melioti*, *Alcaligenes entrophus*, *Clavibacter xyli* and *Azotobacter vinelandii* and phytosphere yeast species such as *Rhodotorula rubra*, *R. glutinis*, *R. marina*, *R. aurantiaca*, *Cryptococcus albidus*, *C. diffluens*, *C. laurentii*, *Saccharomyces rosei*, *S. pretoriensis*, *S. cerevisiae*, *Sporobolomyces roseus*, *S. odorus*, *Kluyveromyces veronae*, and *Aureobasidium pollulans*. Of particular interest are the pigmented microorganisms.

A number of ways are available for introducing a gene expressing the Cyt1A variant polypeptide into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook; Maniatis et al. (Cold Spring Harbor Laboratory Press, Cold Spring Harbor, N.Y.); Davis et al., eds. (1980) *Advanced Bacterial Genetics* (Cold Spring Harbor Laboratory Press, Cold Spring Harbor, N.Y.) and the references cited therein.

Suitable host cells, where the Cyt1A variant polypeptide-containing cells will be treated to prolong the activity of the Cyt1A variant polypeptides in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia*, *Erwinia*, *Shigella*, *Salmonella*, and *Proteus*; Bacillaceae; Rhizobiaceae, such as *Rhizobium*; Spirillaceae, such as photobacterium, *Zymomonas*, *Serratia*, *Aeromonas*, *Vibrio*, *Desulfovibrio*, *Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula*, *Aureobasidium*, *Sporobolomyces*, and the like.

Characteristics of particular interest in selecting a host cell for purposes of Cyt1A variant polypeptide production include ease of introducing the Cyt1A variant polypeptide gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp. (such as *S. cerevisiae*), *Sporobolomyces* spp., phylloplane organisms such as *Pseudomonas* spp. (such as *P. aeruginosa*, *P. fluorescens*), *Erwinia* spp., and *Flavobacterium* spp., and other such organisms, including Bt, *E. coli*, *Bacillus subtilis*, and the like.

Genes encoding the Cyt1A variant polypeptides of the embodiments can be introduced into microorganisms that multiply on plants (epiphytes) to deliver Cyt1A variant polypeptides to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the Cyt1A variant polypeptides of the embodiments can be introduced into a root-colonizing *Bacillus cereus* by standard methods known in the art.

Genes encoding Cyt1A variant polypeptides can be introduced, for example, into the root-colonizing *Bacillus* by means of electrotransformation. Specifically, genes encoding the Cyt1A variant polypeptides can be cloned into a shuttle vector, for example, pHT3101 (Lerecius et al. (1989) *FEMS Microbiol. Letts.* 60: 211-218. The shuttle vector pHT3101 containing the coding sequence for the particular Cyt1A variant polypeptide gene can, for example, be transformed into the root-colonizing *Bacillus* by means of electroporation (Lerecius et al. (1989) *FEMS Microbiol. Letts.* 60: 211-218).

Expression systems can be designed so that Cyt1A variant polypeptides are secreted outside the cytoplasm of gram-negative bacteria, such as *E. coli*, for example. Advantages of having Cyt1A variant polypeptides secreted are: (1) avoidance of potential cytotoxic effects of the Cyt1A variant polypeptide expressed; and (2) improvement in the efficiency of purification of the Cyt1A variant polypeptide, including, but not limited to, increased efficiency in the recovery and purification of the protein per volume cell broth and decreased time and/or costs of recovery and purification per unit protein.

Cyt1A variant polypeptides can be made to be secreted in *E. coli*, for example, by fusing an appropriate *E. coli* signal peptide to the amino-terminal end of the Cyt1A variant polypeptide. Signal peptides recognized by *E. coli* can be found in proteins already known to be secreted in *E. coli*, for example the OmpA protein (Ghrayeb et al. (1984) *EMBO* 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

Cyt1A variant polypeptides of the embodiments can be fermented in a bacterial host and the resulting bacteria processed and used as a microbial spray in the same manner that Bt strains have been used as insecticidal sprays. In the case of a Cyt1A variant polypeptide(s) that is secreted from *Bacillus*, the secretion signal is removed or mutated using procedures known in the art. Such mutations and/or deletions prevent secretion of the Cyt1A variant polypeptide(s) into the growth medium during the fermentation process. The Cyt1A variant polypeptides are retained within the cell, and the cells are then processed to yield the encapsulated Cyt1A variant polypeptides. Any suitable microorganism can be used for this purpose. *Pseudomonas* has been used to express Bt toxins as encapsulated proteins and the resulting cells processed and sprayed as an insecticide (Gaertner et al. (1993), in: *Advanced Engineered Pesticides*, ed. Kim).

Alternatively, the Cyt1A variant polypeptides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated Cyt1A variant polypeptides may then be formulated in accordance with conventional techniques for application to the environment hosting a target pest, e.g., soil, water, and foliage of plants. See, for example EP0192319, and the references cited therein.

In the embodiments, a transformed microorganism (which includes whole organisms, cells, spore(s), Cyt1A variant polypeptide(s), pesticidal component(s), pest-impacting component(s), variant(s), living or dead cells and cell components, including mixtures of living and dead cells and cell components, and including broken cells and cell components) or an isolated Cyt1A variant polypeptide can be formulated with an acceptable carrier into a pesticidal composition(s) that is, for example, a suspension, a solution, an emulsion, a dusting powder, a dispersible granule or pellet, a wettable powder, and an emulsifiable concentrate, an aerosol or spray, an impregnated granule, an adjuvant, a coatable paste, a colloid, and also encapsulations in, for example, polymer substances. Such formulated compositions may be prepared by such conventional means as desiccation, lyophilization, homogenization, extraction, filtration, centrifugation, sedimentation, or concentration of a culture of cells comprising the polypeptide.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the embodiments are normally applied in the form of compositions and can be applied to the crop area, plant, or seed to be treated. For example, the compositions of the embodiments may be applied to grain in preparation for or during storage in a grain bin or silo, etc. The compositions of the embodiments may be applied simultaneously or in succession with other compounds. Methods of applying an active ingredient of the embodiments or an agrochemical composition of the embodiments that contains at least one of the Cyt1A variant polypeptides produced by the bacterial strains of the embodiments include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the embodiments can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and Cyt1A variant polypeptides of the embodiments, can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The compositions (including the transformed microorganisms and Cyt1A variant polypeptides of the embodiments) can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the Cyt1A variant polypeptide and/or transformed microorganisms of the embodiments may be mixed with grain to protect the grain during storage. It is generally important to obtain good control of pests in the early stages of plant growth, as this is the time when the plant can be most severely damaged. The compositions of the embodiments can conveniently contain another insecticide if this is thought necessary. In one embodiment, the composition is applied directly to the soil, at a time of planting, in granular form of a composition of a carrier and dead cells of a *Bacillus* strain or transformed microorganism of the embodiments. Another embodiment is a granular form of a composition comprising an agrochemical such as, for example, an herbicide, an insecticide, a fertilizer, an inert carrier, and dead cells of a *Bacillus* strain or transformed microorganism of the embodiments.

Those skilled in the art will recognize that not all compounds are equally effective against all pests. Compounds of the embodiments display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); Egira (Xylomyges) curialis Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Mamestra configurata* Walker (bertha armyworm); *M. brassicae* Linnaeus (cabbage moth); *Melanchra picta* Harris (zebra caterpillar); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hübner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm);

*Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit *tortrix* moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermuller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); M *hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape *colaspis*); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Gain (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca* domestica Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); *Cimicidae* spp.; *Coreidae* spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schäffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); *Pyrrhocoridae* spp.; *Quadraspidiotus perniciosus* Comstock (San Jose scale); *Reduviidae* spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tinidae* spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as Aceria tosichella Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cylindrotermes nordenskioeldi* Holmgren and *Pseudacanthotermes militaris* Hagen (sugarcane termite). Insects of the order Thysanoptera are also of interest, including but not limited to *thrips*, such as *Stenchaetothrips minutus* van Deventer (sugarcane *thrips*).

Insect pests may be tested for pesticidal activity of compositions of the embodiments in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83(6): 2480-2485. Methods of rearing insect larvae and performing bioassays are well known to one of ordinary skill in the art.

A wide variety of bioassay techniques are known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time. Bioassays described herein can be used with any feeding insect pest in the larval or adult stage.

The following examples are presented by way of illustration, not by way of limitation.

EXAMPLES

Example 1. Creation of Cyt1Aa α-A Variants

To determine the role of Cyt1Aa helix α-A ($^{49}$PNYILQAIMLANAFQNAL$^{66}$—amino acids 49-66 of SEQ ID NO: 2) in Cyt1Aa oligomerization the amino acid residues L58, A59, A61 and F62 located in the hydrophobic phase of the helix were mutated. Mutagenesis was performed by using QuikChange® XL Site-Directed kit (Stratagene La Jolla, Calif.). The sequences of mutagenic oligonucleotides synthesized by Sigma-Aldrich (St Louis, Mo.) are shown in Table 1. Variants were transformed in *E. coli* X-L1 blue strain selected in LB Ampicillin 100 µg/ml at 25° C. Plasmid DNA was extracted from selected colonies using a DNA extraction kit (Qiagen, Hilden, Germany) and sequenced. These plasmids were transformed into Bt 407 strain and selected in LB erythromycin 10 µg/ml at 30° C. The sequence of selected clones was confirmed after PCR amplification of the selected colonies using IRE1d-IRE4r oligonucleotides that amplify a fragment of 750 pb of cyt1Aa gene (Table 1).

TABLE 1

| Oligo | DNA sequence | SEQ ID NO: |
|---|---|---|
| A59C | TTGCAAGCAATTATGTTATGTAATGCCTTTCAAAATGC | 20 |
| A61C | GCAAGCAATTATGTTAGCAAACTGTTTTCAAAATGCATTAGTTCCC | 21 |
| L58E | TATATATTGCAAGCAATTATGGAAGCAAATGCGTTTCAAAATGC | 22 |
| A59E | TATATTGCAAGCAATTATGTTAGAAAATGCGTTTCAAATGC | 23 |

TABLE 1-continued

| Oligo | DNA sequence | SEQ ID NO: |
|---|---|---|
| F62R | AGCAATTATGTTAGCAAATGCACGGCAAAATGCGTTAGTTCC | 24 |
| [RE1d | TGTGAATTCATGGAAAATTTAAATCATTG | 25 |
| [RE4r | CTACTCGAGGAGGGTTCCATTAATAGC | 26 |

Cyt1Aa (SEQ ID NO: 2) or Cry11Aa (SEQ ID NO: 13) protoxins were produced in *B. thuringiensis* 407 acrystalliferous strain transformed with plasmid pWF45 (Wu et al., *Mol Microbiol* 13: 965-972, 1994) or pCG6 (Chang et al., *Appl Environ Microbiol* 59: 815-821, 1993). Cyt1Aa variants were also expressed in the *B. thuringiensis* 407 acrystalliferous strain. Bt strains expressing Cyt or Cry11Aa proteins were grown four days at 30° C. in solid nutrient broth sporulation medium supplemented with 10 µg/ml erythromycin for Cyt1Aa (SEQ ID NO: 2) or 25 µg/ml erythromycin for Cry11Aa (SEQ ID NO: 13) (Lereclus et al., *Bio/Technology* 13: 67-71 1995). Spores and crystals were washed three times with 0.3 M NaCl, 0.01 M EDTA, pH 8.0 by centrifugation for 10 min at 10,000 rpm at 4° C., the crystal were separated from the spores by density gradient centrifugation, and the crystal suspension stored at −20° C. Cyt1A proteins were solubilized 1h at 37° C. in 50 mM Na$_2$CO$_3$, 10 mM DTT, pH 10.5, agitation at 350 rpm and centrifuged for 10 min at 10,000 rpm 4° C. The soluble protoxins were recovered in the supernatant. Protein concentrations were determined by the Bradford assay. Finally, Cyt1Aa (SEQ ID NO: 2) protoxin was activated with trypsin 1:20 (Trypsin: Cyt1Aa) ratio (Sigma-Aldrich Co., St Louis, Mo.) w/w for 2 h at 30° C. Variants A59E (SEQ ID NO: 17) and F62R (SEQ ID NO: 19) were not produced. The variant L58E (SEQ ID NO: 15) produced lower levels of the mutated protoxin compared to Cyt1Aa (SEQ ID NO: 2) producing strain. However, after solubilization of protein crystals by alkaline treatment the L58E protein (SEQ ID NO: 15) was not solubilized (data not shown). Therefore the A59E, F62R and L58E α-A variants were not further analyzed. In contrast the Cyt1Aa-A59C variant (SEQ ID NO: 4) and the Cyt1Aa-A61C variant (SEQ ID NO: 6) produced a 27 kDa protein upon sporulation and when these proteins were solubilized and treated with trypsin for toxin activation, yielded a 22 kDa protein indicating no major structural changes (data not shown).

Example 2. Effect of Cyt1Aa-A59C and Cyt1Aa-A61C on Toxin Oligomerization

To determine the effect of the Cyt1Aa-A59C variant (SEQ ID NO: 4) and the Cyt1Aa-A61C variant (SEQ ID NO: 6) on Cyt1Aa oligomerization, soluble protoxins of Cyt1Aa (SEQ ID NO: 2), the Cyt1Aa-A59C variant (SEQ ID NO: 4), and the Cyt1Aa-A61C variant (SEQ ID NO: 6) were incubated with small unilaminar vesicles (SUV) and trypsin, the membrane pellet was separated by centrifugation and analyzed by western blot using an anti-Cyt1Aa antibody. Small unilaminar vesicles (SUV) were prepared as follows: Briefly, egg-yolk phosphatidyl choline (PC), cholesterol (Ch) (Avanti Polar Lipids, Alabaster, Ala.) and stearylamine (S) (Sigma-Aldrich, St Louis, Mo.) from chloroform stocks, were mixed in glass vials in a 10:3:1 proportion, respectively, at 0.65 µmol final concentration of the total lipid mixture and dried by nitrogen flow evaporation, followed by overnight storage under vacuum to remove residual chloroform. The lipids were hydrated in 0.65 ml of 10 mM CHES, 150 mM KCl pH 9 by a 30 min incubation followed by vortex. To prepare SUV the lipid suspension was sonicated three to five times during 20 sec each in a Branson-1200 bath sonicator (AMINCO® AMERICAN INSTRUMENT COMPANY Danbury, Conn.). SUV were used the same day upon their preparation. Oligomerization of Cyt1Aa and variants was performed as previously described (Lopez-Diaz et al., Environm Microbiol. 15: 330-3039 2013). Briefly oligomerization was performed in a final volume of 100 µl by incubation of 200 ng of Cyt1Aa solubilized protoxin, or that of the Cyt1Aa-A59C variant (SEQ ID NO: 4) and the Cyt1Aa-A61C variant (SEQ ID NO: 6) with 90 µl SUV liposomes and 10 ng of trypsin during 2h at 30° C. and agitation at 350 rpm. 1 mM PMSF was added to stop the reaction. Samples were centrifuged 30 min at 55,000 rpm to separate the membrane pellet from the supernatant, heated at 65° C. for 3 min, loaded in SDS-PAGE gels and transferred to PVDF Immobilon®-P Millipore membranes in a wet chamber during 12 h, 150 mA, at 4° C. The PVDF membrane was blocked with 5% skimmed milk in PBS for 1h at room temperature with slow agitation and washed two times 5 min with PBS containing 0.1% Tween® 20 (PBS-Tween®). The membrane was then incubated in PBS-Tween® containing polyclonal anti-Cyt1A antibody (1:30,000 dilution) for 1h at room temperature, washed twice with PBS-Tween® for 5 min and then incubated with goat anti-rabbit antibody coupled to horseradish peroxidase (Santa Cruz Biotechnology, Dallas, Tex.) (1:10000 dilution in PBS-Tween®). Finally the peroxidase signal was visualized with SuperSignal™ chemiluminescent substrate (ECL; Amersham Pharmacia Biotech). Oligomerization assays were performed at least five times with different preparations of the Cyt1Aa (SEQ ID NO: 2), Cyt1Aa-A59C variant (SEQ ID NO: 4) or the Cyt1Aa-A61C variant (SEQ ID NO: 6) and different SUV preparations. Molecular weight markers were Precision Plus Protein™ Standards All Blue (Bio-Rad) and molecular masses are indicated in kDa.

Cyt1Aa (SEQ ID NO: 2), the Cyt1Aa-A59C variant (SEQ ID NO: 4), and the Cyt1Aa-A61C variant (SEQ ID NO: 6) produced high molecular weight oligomers after protease activation in the presence of synthetic membranes (data not shown). This result shows that Cyt1Aa-A59C and Cyt1Aa-A61C mutations did not affect toxin oligomerization.

Example 3. Insecticidal Activity of Cyt1Aa α-A Variants Against *Aedes aegypti*

To determine the effect of the α-A mutations on activity, the insecticidal activity of Cyt1Aa (SEQ ID NO: 2), the Cyt1Aa-A59C variant (SEQ ID NO: 4), and the Cyt1Aa-A61C variant (SEQ ID NO: 6) was determined against *Aedes aegypti* larvae. The Cyt1Aa proteins were assayed against *Aedes aegypti* mosquitoes as follows: *Aedes aegypti* mosquitoes were reared at 28° C., 75% humidity and a 12h:12h light: dark photoperiod. Mosquitocidal bioassays were performed against 10 early $4^{th}$-instar larvae in 100 ml of dechlorinated water. Ten different concentrations (50 to 10000 ng/ml) of spore/crystal suspensions of Cyt1Aa (SEQ ID NO: 2) or variants were sonicated for 1 min in an ultrasonic processor (Cole-Palmer) and immediately diluted into 100 ml water containers. Negative control (dechlorinated water) was included in the bioassay, and larvae viability examined 24 h after treatment. The mean lethal concentration ($LC_{50}$) was determined by Probit analysis using statistical parameters using data obtained from three independent assays (PoloPlus© LeOra Software Company®, Petaluma, Calif.). Table 2 shows the $LC_{50}$ values of toxicity of Cyt1Aa (SEQ ID NO: 2), Cyt1Aa-A59C variant (SEQ ID NO: 4), and Cyt1Aa-A61C variant (SEQ ID NO: 6) to *Aedes aegypti* larvae. Cyt1Aa-A59C variant (SEQ ID NO: 2) showed two-fold lower insecticidal activity compared to Cyt1Aa (SEQ ID NO: 2) while Cyt1Aa-A61C variant (SEQ ID NO: 6) showed five-fold higher insecticidal activity against *Aedes aegypti* (Table 2).

TABLE 2

| Toxin | LC5 in [ng/ml] |
| --- | --- |
| Cyt1Aa (SEQ ID NO: 2) | 1100 (880-1480)[a] |
| Cyt1Aa-A59C (SEQ ID NO: 4) | 2419 (1861-3653) |
| Cyt1Aa-A61C (SEQ ID NO: 6) | 212 (131-273) |
| Cry11Aa | 669 (476-994) |

[a] 95% confidential limits calculated by Probit statistical analysis.

Example 4. Synergy of Cyt1Aa α-A Variants with Cry11Aa

The capacity of Cyt1Aa (SEQ ID NO: 2), the Cyt1Aa-A59C variant (SEQ ID NO: 4), and the Cyt1Aa-A61C variant (SEQ ID NO: 6) to synergize Cry11Aa toxicity to *A. aegypti* larvae was also determined as previously described (Fernandez-Luna et al., 2010) by testing for deviation from the null hypothesis of simple independent action, which assumes the proportion of larvae surviving to the exposure of mixture of toxins is the product of the proportions of larvae that survive to the exposure of each toxin separately. Briefly, the formula $S_{(ab)EXP} = S_{(a)OBS} \times S_{(b)OBS}$ (Fernandez-Luna et al., *J Invertebr Pathol* 104: 231-233 2010) was used, where $S_{(ab)EXP}$ is the proportion of larvae expected to survive to the exposure of a mixture of toxins a and b, $S_{(a)OBS}$ and $S_{(b)OBS}$ are the observed proportion of larvae that survived to the exposure to toxin a or toxin b, respectively. Thirty larvae were used per toxin and per mixture of toxins. The expected mortality for larvae that were exposed to the mixture of toxins a and b was calculated as $(1-S_{(ab)EXP}) \times 100\%$ and the expected numbers of dead and live larvae were calculated by multiplying the expected mortality and survival rates by the sample size used when each toxin was tested separately. These assays were done by triplicate. Finally the Fisher's exact test was used to determine if a significant difference occurred between observe and expected mortality data. Mixtures of Cyt1Aa (SEQ ID NO: 2) and Cry11Aa were prepared that would give a toxicity of 20% based on their corresponding $LC_{50}$ toxicity values. Table 3 shows that Cyt1Aa-A59C variant (SEQ ID NO: 4) and Cyt1Aa-A61C variant (SEQ ID NO: 6) are able to synergize the activity of Cry11Aa since the toxicity of the protein mixtures showed a three to four-fold higher toxicity than the expected mortality.

TABLE 3

| protein | $S_{(toxin)OBS}{}^a =$ (Rep1 + Rep2 + Rep3)/n | $S_{(Cyt1Aa, Cry11Aa)EXP}{}^b = S_{(Cyt1Aa)OBS} \times S_{(Cry11Aa)OBS}$ | Expected mortality$^c$ = $(1 - S_{(Cyt1Aa, Cry11Aa)EXP}) \times 100\%$ | Observed mortality$^d$ Cyt1Aa+Cry11Aa |
|---|---|---|---|---|
| Cyt1Aa (SEQ ID NO: 2) | 1.00 | 0.80 | 20% | 90 ± 10% |
| A59C | 1.00 | 0.80 | 20% | 57 ± 20% |
| A61C | 0.93 | 0.75 | 25.3% | 83 ± 15% |
| Cry11Aa | 0.80 | | | |

$^a$ Observed survival of individual toxin $S_{(toxin)OBS}$ corresponds to the observed proportion of larvae that survived to the exposure to Cyt1Aa or Cyt1A variant. Observed mortality was 20% with Cry11Aa at 200 ng per ml and 0% with Cyt1Aa at 75 ng Cyt1Aa per ml. n = 30 larvae for each toxin tested.

Example 5. Hemolytic Activity of Cyt1Aa α-A Variants

The hemolytic activity of Cyt1Aa, the Cyt1Aa-A59C variant (SEQ ID NO: 4), and the Cyt1Aa-A61C variant (SEQ ID NO: 6) was determined by incubating rabbit red blood cells with increasing concentrations of trypsin-activated toxins as previously described (Rodriguez-Almazan et al., Biochemistry 50: 388-396 2011). Briefly, rabbit red blood cells were washed three times in buffer A (0.1 M dextrose, 0.07 M NaCl, 0.02 M sodium citrate, 0.002 M citrate, pH 7.4) and diluted to a concentration of $2 \times 10^8$ cells/ml in the same buffer. A final volume of reaction mixtures of 0.2 ml containing 20 µl of washed blood cells and various concentrations of Cyt1Aa toxin (20-1200 ng) in the same buffer were incubated at 37° C. for 30 min in 96 wells microtiter plates. The supernatants were collected in a new microtiter plate by centrifugation at 2,500-xg for 5 min at 4° C. and hemolytic activity was quantitated measuring the absorbance of the supernatant at 405 nm. Positive control showing 100 percent hemolysis was defined after incubation of the same volume of rabbit red blood cells with dechlorinated $H_2O$. Negative controls were red blood cells incubated with buffer A. These assays were performed three times in triplicate each time. A t-test was performed using the statistical program GraphPad Prism®. FIG. 6 shows that both α-A variants were severely affected in hemolysis since wild type Cyt1Aa toxin showed a fifty percent effective dose ($ED_{50}$) of 130 ng/ml while Cyt1Aa-A61C variant (SEQ ID NO: 6) lysed only 40% of the red blood cells with 1200 ng/ml and the Cyt1Aa-A59C variant (SEQ ID NO: 4) showed null hemolytic activity at the highest toxin concentration tested.

Example 6. Agrobacterium-Mediated Transformation of Maize and Regeneration of Transgenic Plants For Agrobacterium-mediated transformation of maize with a polynucleotide (e.g., SEQ ID NO: 1, SEQ ID NO: 3, SEQ ID NO: 5), the method of Zhao can be used (U.S. Pat. No. 5,981,840 and PCT patent publication WO98/32326; the contents of which are hereby incorporated by reference). Briefly, immature embryos are isolated from maize and the embryos contacted with a suspension of Agrobacterium under conditions whereby the bacteria are capable of transferring the polynucleotide (SEQ ID NO: 1, SEQ ID NO: 3, SEQ ID NO: 5) to at least one cell of at least one of the immature embryos (step 1: the infection step). In this step the immature embryos can be immersed in an Agrobacterium suspension for the initiation of inoculation. The embryos are co-cultured for a time with the Agrobacterium (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). The immature embryos can be cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 7. Transformation of Soybean Embryos

Soybean embryos are bombarded with a plasmid containing the polynucleotide of SEQ ID NO: 1, SEQ ID NO: 3, SEQ ID NO: 5 operably linked to a suitable promoter as follows. To induce somatic embryos, cotyledons, 3-5 mm in length dissected from surface-sterilized, immature seeds of an appropriate soybean cultivar are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation includes, but is not limited to: the 35S promoter from Cauliflower Mosaic Virus (Odell, et al., (1985) Nature 313:810-812), the hygromycin phosphotransferase gene from plasmid pJR225 (from E. coli; Gritz, et al., (1983) Gene 25:179-188), and the 3' region of the nopaline synthase gene from the T DNA of the Ti plasmid of Agrobacterium tumefaciens. The expression cassette comprising a polynucleotide (e.g., SEQ ID NO: 1) operably linked to a suitable promoter can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1M), and 50 μL CaCl2 (2.5M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications, patents and patent applications mentioned in the specification are indicative of the level of those skilled in the art to which this invention pertains. All publications, patents and patent applications are herein incorporated by reference to the same extent as if each individual publication, patent or patent application was specifically and individually indicated to be incorporated by reference.

Although the foregoing invention has been described in some detail by way of illustration and example for purposes of clarity of understanding, it will be obvious that certain changes and modifications may be practiced within the scope of the embodiments.

SEQUENCE LISTING

<160> NUMBER OF SEQ ID NOS: 26

<210> SEQ ID NO 1
<211> LENGTH: 747
<212> TYPE: DNA
<213> ORGANISM: Bacillus thuringiensis

<400> SEQUENCE: 1

```
atggaaaatt taaatcattg tccattagaa gatataaagg taaatccatg gaaaacccct      60
caatcaacag caagggttat tac

```
Trp Lys Thr Pro Gln Ser Thr Ala Arg Val Ile Thr Leu Arg Val Glu
            20                  25                  30

Asp Pro Asn Glu Ile Asn Asn Leu Leu Ser Ile Asn Glu Ile Asp Asn
        35                  40                  45

Pro Asn Tyr Ile Leu Gln Ala Ile Met Leu Ala Asn Ala Phe Gln Asn
    50                  55                  60

Ala Leu Val Pro Thr Ser Thr Asp Phe Gly Asp Ala Leu Arg Phe Ser
65                  70                  75                  80

Met Pro Lys Gly Leu Glu Ile Ala Asn Thr Ile Thr Pro Met Gly Ala
                85                  90                  95

Val Val Ser Tyr Val Asp Gln Asn Val Thr Gln Thr Asn Asn Gln Val
            100                 105                 110

Ser Val Met Ile Asn Lys Val Leu Glu Val Leu Lys Thr Val Leu Gly
        115                 120                 125

Val Ala Leu Ser Gly Ser Val Ile Asp Gln Leu Thr Ala Ala Val Thr
    130                 135                 140

Asn Thr Phe Thr Asn Leu Asn Thr Gln Lys Asn Glu Ala Trp Ile Phe
145                 150                 155                 160

Trp Gly Lys Glu Thr Ala Asn Gln Thr Asn Tyr Thr Tyr Asn Val Leu
                165                 170                 175

Phe Ala Ile Gln Asn Ala Gln Thr Gly Gly Val Met Tyr Cys Val Pro
            180                 185                 190

Val Gly Phe Glu Ile Lys Val Ser Ala Val Lys Glu Gln Val Leu Phe
        195                 200                 205

Phe Thr Ile Gln Asp Ser Ala Ser Tyr Asn Val Asn Ile Gln Ser Leu
    210                 215                 220

Lys Phe Ala Gln Pro Leu Val Ser Ser Ser Gln Tyr Pro Ile Ala Asp
225                 230                 235                 240

Leu Thr Ser Ala Ile Asn Gly Thr Leu
                245
```

<210> SEQ ID NO 3
<211> LENGTH: 747
<212> TYPE: DNA
<213> ORGANISM: Artificial Sequence
<220> FEATURE:
<223> OTHER INFORMATION: Cyt1Aa variant

<400> SEQUENCE: 3

```
atggaaaatt taaatcattg tccattagaa gatataaagg taaatccatg gaaaacccct     60
caatcaacag caagggttat tacattacgt gttgaggatc caaatgaaat caataatctt    120
ctttctatta acgaaattga taatccgaat tatatattgc aagcaattat gttatgtaat    180
gcatttcaaa atgcattagt tcccacttct acagattttg gtgatgccct acgctttagt    240
atgccaaaag gtttagaaat cgcaaacaca attacaccga tgggtgctgt agtgagttat    300
gttgatcaaa atgtaactca aacgaataac caagtaagtg ttatgattaa taaagtctta    360
gaagtgttaa aaactgtatt aggagttgca ttaagtggat ctgtaataga tcaattaact    420
gcagcagtta caaatacgtt tacaaattta aatactcaaa aaaatgaagc atggattttc    480
tggggcaagg aaactgctaa tcaaacaaat tacacataca atgtcctgtt tgcaatccaa    540
aatgcccaaa ctggtggcgt tatgtattgt gtaccagttg gttttgaaat taaagtatca    600
gcagtaaagg aacaagtttt atttttcaca attcaagatt ctgcgagcta caatgttaac    660
atccaatctt tgaaatttgc acaaccatta gttagctcaa gtcagtatcc aattgcagat    720
```

```
cttactagcg ctattaatgg aaccctc                                         747
```

<210> SEQ ID NO 4
<211> LENGTH: 249
<212> TYPE: PRT
<213> ORGANISM: Artificial Sequence
<220> FEATURE:
<223> OTHER INFORMATION: Cyt1Aa variant

<400> SEQUENCE: 4

Met Glu Asn Leu Asn His Cys Pro Leu Glu Asp Ile Lys Val Asn Pro
1               5                   10                  15

Trp Lys Thr Pro Gln Ser Thr Ala Arg Val Ile Thr Leu Arg Val Glu
            20                  25                  30

Asp Pro Asn Glu Ile Asn Asn Leu Leu Ser Ile Asn Glu Ile Asp Asn
35 40 45

Pro Asn Tyr Ile Leu Gln Ala Ile Met Leu Cys Asn Ala Phe Gln Asn
50 55 60

Ala Leu Val Pro Thr Ser Thr Asp Phe Gly Asp Ala Leu Arg Phe Ser
65 70 75 80

Met Pro Lys Gly Leu Glu Ile Ala Asn Thr Ile Thr Pro Met Gly Ala
85 90 95

Val Val Ser Tyr Val Asp Gln Asn Val Thr Gln Thr Asn Asn Gln Val
100 105 110

Ser Val Met Ile Asn Lys Val Leu Glu Val Leu Lys Thr Val Leu Gly
115 120 125

Val Ala Leu Ser Gly Ser Val Ile Asp Gln Leu Thr Ala Ala Val Thr
130 135 140

Asn Thr Phe Thr Asn Leu Asn Thr Gln Lys Asn Glu Ala Trp Ile Phe
145 150 155 160

Trp Gly Lys Glu Thr Ala Asn Gln Thr Asn Tyr Thr Tyr Asn Val Leu
165 170 175

Phe Ala Ile Gln Asn Ala Gln Thr Gly Gly Val Met Tyr Cys Val Pro
180 185 190

Val Gly Phe Glu Ile Lys Val Ser Ala Val Lys Glu Gln Val Leu Phe
195 200 205

Phe Thr Ile Gln Asp Ser Ala Ser Tyr Asn Val Asn Ile Gln Ser Leu
210 215 220

Lys Phe Ala Gln Pro Leu Val Ser Ser Ser Gln Tyr Pro Ile Ala Asp
225 230 235 240

Leu Thr Ser Ala Ile Asn Gly Thr Leu
245

<210> SEQ ID NO 5
<211> LENGTH: 747
<212> TYPE: DNA
<213> ORGANISM: Artificial Sequence
<220> FEATURE:
<223> OTHER INFORMATION: Cyt1Aa variant

<400> SEQUENCE: 5
atggaaaatt taaatcattg tccattagaa gatataaagg taaatccatg gaaaacccct 60
caatcaacag caagggttat tacattacgt gttgaggatc caaatgaaat caataatctt 120
ctttctatta acgaaattga taatccgaat tatatattgc aagcaattat gttagcaaat 180
tgttttcaaa atgcattagt tcccacttct acagattttg gtgatgccct acgctttagt 240

-continued

```
atgccaaaag gtttagaaat cgcaaacaca attacaccga tgggtgctgt agtgagttat    300
gttgatcaaa atgtaactca aacgaataac caagtaagtg ttatgattaa taaagtctta    360
gaagtgttaa aaactgtatt aggagttgca ttaagtggat ctgtaataga tcaattaact    420
gcagcagtta caaatacgtt tacaaattta aatactcaaa aaatgaagc atggattttc     480 tggggcaagg aaactgctaa tcaaacaaat tacacataca atgtcctgtt tgcaatccaa    540
aatgcccaaa ctggtggcgt tatgtattgt gtaccagttg gttttgaaat taaagtatca    600
gcagtaaagg aacaagtttt atttttcaca attcaagatt ctgcgagcta caatgttaac    660
atccaatctt tgaaatttgc acaaccatta gttagctcaa gtcagtatcc aattgcagat    720
cttactagcg ctattaatgg aaccctc                                        747
```

<210> SEQ ID NO 6
<211> LENGTH: 249
<212> TYPE: PRT
<213> ORGANISM: Artificial Sequence
<220> FEATURE:
<223> OTHER INFORMATION: Cyt1Aa variant

<400> SEQUENCE: 6

```
Met Glu Asn Leu Asn His Cys Pro Leu Glu Asp Ile Lys Val Asn Pro
1               5                   10                  15

Trp Lys Thr Pro Gln Ser Thr Ala Arg Val Ile Thr Leu Arg Val Glu
            20                  25                  30

Asp Pro Asn Glu Ile Asn Asn Leu Leu Ser Ile Asn Glu Ile Asp Asn
        35                  40                  45

Pro Asn Tyr Ile Leu Gln Ala Ile Met Leu Ala Asn Cys Phe Gln Asn
    50                  55                  60

Ala Leu Val Pro Thr Ser Thr Asp Phe Gly Asp Ala Leu Arg Phe Ser
65                  70                  75                  80

Met Pro Lys Gly Leu Glu Ile Ala Asn Thr Ile Thr Pro Met Gly Ala
                85                  90                  95

Val Val Ser Tyr Val Asp Gln Asn Val Thr Gln Thr Asn Asn Gln Val
            100                 105                 110

Ser Val Met Ile Asn Lys Val Leu Glu Val Leu Lys Thr Val Leu Gly
        115                 120                 125

Val Ala Leu Ser Gly Ser Val Ile Asp Gln Leu Thr Ala Ala Val Thr
130                 135                 140

Asn Thr Phe Thr Asn Leu Asn Thr Gln Lys Asn Glu Ala Trp Ile Phe
145                 150                 155                 160

Trp Gly Lys Glu Thr Ala Asn Gln Thr Asn Tyr Thr Tyr Asn Val Leu
                165                 170                 175

Phe Ala Ile Gln Asn Ala Gln Thr Gly Gly Val Met Tyr Cys Val Pro
            180                 185                 190

Val Gly Phe Glu Ile Lys Val Ser Ala Val Lys Glu Gln Val Leu Phe
        195                 200                 205

Phe Thr Ile Gln Asp Ser Ala Ser Tyr Asn Val Asn Ile Gln Ser Leu
    210                 215                 220

Lys Phe Ala Gln Pro Leu Val Ser Ser Gln Tyr Pro Ile Ala Asp
225                 230                 235                 240

Leu Thr Ser Ala Ile Asn Gly Thr Leu
                245
```

<210> SEQ ID NO 7
<211> LENGTH: 250

<212> TYPE: PRT
<213> ORGANISM: Bacillus thuringiensis

<400> SEQUENCE: 7

```
Met Glu Asn Pro Asn His Cys Pro Leu Glu Asp Ile Gln Val Asn Pro
1               5                   10                  15

Trp Lys Thr Pro Gln Ser Lys Ala Arg Val Ile Thr Leu Arg Ile Asp
            20                  25                  30

Asp Pro Asn Glu Ile Asn Asn Leu Leu Ser Ile Asn Glu Ile Glu Asn
        35                  40                  45

Thr Asn Tyr Leu Leu Gln Ala Ile Met Leu Ala Asn Ala Phe Gln Lys
    50                  55                  60

Ala Leu Val Pro Thr Ser Thr Glu Phe Ala Glu Asp Ala Leu Gln Phe
65                  70                  75                  80

Ser Met Thr Lys Gly Leu Glu Val Ala Asn Thr Ile Ser Pro Pro Gly
                85                  90                  95

Ala Val Val Gln Tyr Val Asp Gln Asn Val Ser Gln Thr Asn Asn Gln
            100                 105                 110

Val Ser Ala Met Ile Asn Lys Val Leu Asp Val Leu Lys Ser Ile Leu
        115                 120                 125

Gly Val Ala Leu Gly Gln Ser Val Ile Glu Gln Leu Thr Ser Ala Val
    130                 135                 140

Thr Asn Thr Phe Thr Asn Leu Asn Thr Gln Lys Asn Glu Ala Trp Ile
145                 150                 155                 160

Phe Trp Gly Arg Glu Thr Ser Thr Gln Thr Asn Tyr Thr Tyr Asn Val
                165                 170                 175

Leu Phe Ala Ile Gln Asn Gly Gln Thr Gly Gly Val Met Tyr Cys Val
            180                 185                 190

Pro Val Gly Phe Glu Ile Lys Val Ser Ala Val Lys Glu Arg Val Leu
        195                 200                 205

Phe Leu Thr Ile Gln Asp Ser Ala Ser Tyr Asn Val Asn Ile Gln Ser
    210                 215                 220

Leu Lys Phe Ala Gln Pro Leu Val Ser Ala Ser Glu Tyr Pro Ile Ala
225                 230                 235                 240

Asp Leu Thr Ser Ala Ile Asn Gly Thr Leu
                245                 250
```

<210> SEQ ID NO 8
<211> LENGTH: 265
<212> TYPE: PRT
<213> ORGANISM: Bacillus thuringiensis

<400> SEQUENCE: 8

```
Met Lys Glu Ser Ile Tyr Tyr Asn Glu Glu Asn Glu Ile Gln Ile Ser
1               5                   10                  15

Gln Gly Asn Cys Phe Pro Glu Glu Leu Gly His Asn Pro Trp Arg Gln
            20                  25                  30

Pro Gln Ser Thr Ala Arg Val Ile Tyr Leu Lys Val Lys Asp Pro Ile
        35                  40                  45

Asp Thr Thr Gln Leu Leu Glu Ile Thr Glu Ile Glu Asn Pro Asn Tyr
    50                  55                  60

Val Leu Gln Ala Ile Gln Leu Ala Ala Ala Phe Gln Asp Ala Leu Val
65                  70                  75                  80

Pro Thr Glu Thr Glu Phe Gly Glu Ala Ile Arg Phe Ser Met Pro Lys
                85                  90                  95
```

-continued

```
Gly Leu Glu Val Ala Lys Thr Ile Gln Pro Lys Gly Ala Val Val Ala
            100                 105                 110

Tyr Thr Asp Gln Thr Leu Ser Gln Ser Asn Asn Gln Val Ser Val Met
        115                 120                 125

Ile Asp Arg Val Ile Ser Val Leu Lys Thr Val Met Gly Val Ala Leu
130                 135                 140

Ser Gly Ser Ile Ile Thr Gln Leu Thr Ala Ala Ile Thr Asp Thr Phe
145                 150                 155                 160

Thr Asn Leu Asn Thr Gln Lys Asp Ser Ala Trp Val Phe Trp Gly Lys
                165                 170                 175

Glu Thr Ser His Gln Thr Asn Tyr Thr Tyr Asn Val Met Phe Ala Ile
            180                 185                 190

Gln Asn Glu Thr Thr Gly Arg Val Met Met Cys Val Pro Ile Gly Phe
        195                 200                 205

Glu Ile Arg Val Phe Thr Asp Lys Arg Thr Val Leu Phe Leu Thr Thr
    210                 215                 220

Lys Asp Tyr Ala Asn Tyr Ser Val Asn Ile Gln Thr Leu Arg Phe Ala
225                 230                 235                 240

Gln Pro Leu Ile Asp Ser Arg Ala Leu Ser Ile Asn Asp Leu Ser Glu
                245                 250                 255

Ala Leu Arg Ser Ser Lys Tyr Leu Tyr
            260                 265

<210> SEQ ID NO 9
<211> LENGTH: 259
<212> TYPE: PRT
<213> ORGANISM: Bacillus thuringiensis

<400> SEQUENCE: 9

Met Tyr Thr Lys Asn Phe Ser Asn Ser Arg Met Glu Val Lys Gly Asn
1               5                   10                  15

Asn Gly Cys Ser Ala Pro Ile Ile Arg Lys Pro Phe Lys His Ile Val
            20                  25                  30

Leu Thr Val Pro Ser Ser Asp Leu Asp Asn Phe Asn Thr Val Phe Tyr
        35                  40                  45

Val Gln Pro Gln Tyr Ile Asn Gln Ala Leu His Leu Ala Asn Ala Phe
    50                  55                  60

Gln Gly Ala Ile Asp Pro Leu Asn Leu Asn Phe Asn Phe Glu Lys Ala
65                  70                  75                  80

Leu Gln Ile Ala Asn Gly Ile Pro Asn Ser Ala Ile Val Lys Thr Leu
                85                  90                  95

Asn Gln Ser Val Ile Gln Gln Thr Val Glu Ile Ser Val Met Val Glu
            100                 105                 110

Gln Leu Lys Lys Ile Ile Gln Glu Val Leu Gly Leu Val Ile Asn Ser
        115                 120                 125

Thr Ser Phe Trp Asn Ser Val Glu Ala Thr Ile Lys Gly Thr Phe Thr
    130                 135                 140

Asn Leu Asp Thr Gln Ile Asp Glu Ala Trp Ile Phe Trp His Ser Leu
145                 150                 155                 160

Ser Ala His Asn Thr Ser Tyr Tyr Tyr Asn Ile Leu Phe Ser Ile Gln
                165                 170                 175

Asn Glu Asp Thr Gly Ala Val Met Ala Val Leu Pro Leu Ala Phe Glu
            180                 185                 190

Val Ser Val Asp Val Glu Lys Gln Lys Val Leu Phe Phe Thr Ile Lys
        195                 200                 205
```

Asp Ser Ala Arg Tyr Glu Val Lys Met Lys Ala Leu Thr Leu Val Gln
            210                 215                 220

Ala Leu His Ser Ser Asn Ala Pro Ile Val Asp Ile Phe Asn Val Asn
225                 230                 235                 240

Asn Tyr Asn Leu Tyr His Ser Asn His Lys Ile Ile Gln Asn Leu Asn
            245                 250                 255

Leu Ser Asn

<210> SEQ ID NO 10
<211> LENGTH: 263
<212> TYPE: PRT
<213> ORGANISM: Bacillus thuringiensis

<400> SEQUENCE: 10

Met His Leu Asn Asn Leu Asn Asn Phe Asn Asn Leu Glu Asn Asn Gly
1               5                   10                  15

Glu Tyr His Cys Ser Gly Pro Ile Ile Lys Lys Pro Phe Arg His Ile
            20                  25                  30

Ala Leu Thr Val Pro Ser Ser Asp Ile Thr Asn Phe Asn Glu Ile Phe
        35                  40                  45

Tyr Val Glu Pro Gln Tyr Ile Ala Gln Ala Ile Arg Leu Thr Asn Thr
    50                  55                  60

Phe Gln Gly Ala Ile Asp Pro Leu Thr Leu Asn Phe Asn Phe Glu Lys
65                  70                  75                  80

Ala Leu Gln Ile Ala Asn Gly Leu Pro Asn Ala Gly Val Thr Gly Thr
                85                  90                  95

Ile Asn Gln Ser Val Ile His Gln Thr Ile Glu Val Ser Val Met Ile
            100                 105                 110

Ser Gln Ile Lys Glu Ile Ile Arg Ser Val Leu Gly Leu Val Ile Asn
        115                 120                 125

Ser Ala Asn Phe Trp Asn Ser Val Val Ser Ala Ile Thr Asn Thr Phe
130                 135                 140

Thr Asn Leu Glu Pro Gln Val Asp Glu Asn Trp Ile Val Trp Arg Asn
145                 150                 155                 160

Leu Ser Ala Thr Gln Thr Ser Tyr Phe Tyr Lys Ile Leu Phe Ser Ile
                165                 170                 175

Gln Asn Glu Asp Thr Gly Arg Phe Met Ala Ile Leu Pro Ile Ala Phe
            180                 185                 190

Glu Ile Thr Val Asp Val Gln Lys Gln Gln Leu Leu Phe Ile Thr Ile
        195                 200                 205

Lys Asp Ser Ala Arg Tyr Glu Val Lys Met Lys Ala Leu Thr Val Val
    210                 215                 220

Gln Ala Leu Asp Ser Tyr Asn Ala Pro Ile Ile Asp Val Phe Asn Val
225                 230                 235                 240

Arg Asn Tyr Ser Leu His Arg Pro Asn His Asn Ile Leu Gln Asn Leu
                245                 250                 255

Asn Val Asn Pro Ile Lys Ser
            260

<210> SEQ ID NO 11
<211> LENGTH: 263
<212> TYPE: PRT
<213> ORGANISM: Bacillus thuringiensis

<400> SEQUENCE: 11

```
Met Tyr Thr Lys Asn Leu Asn Ser Leu Glu Ile Asn Glu Asp Tyr Gln
1               5                   10                  15

Tyr Ser Arg Pro Ile Ile Lys Lys Pro Phe Arg His Ile Thr Leu Thr
            20                  25                  30

Val Pro Ser Ser Asp Ile Ala Ser Phe Asn Glu Ile Phe Tyr Leu Glu
        35                  40                  45

Pro Gln Tyr Val Ala Gln Ala Leu Arg Leu Thr Asn Thr Phe Gln Ala
    50                  55                  60

Ala Ile Asp Pro Leu Thr Leu Asn Phe Asp Phe Glu Lys Ala Leu Gln
65                  70                  75                  80

Ile Ala Asn Gly Leu Pro Asn Ala Gly Ile Thr Gly Thr Leu Asn Gln
                85                  90                  95

Ser Val Ile Gln Gln Thr Ile Glu Ile Ser Val Met Ile Ser Gln Ile
            100                 105                 110

Lys Glu Ile Ile Arg Asn Val Leu Gly Leu Val Ile Asn Ser Thr Asn
                115                 120                 125

Phe Trp Asn Ser Val Leu Ala Ala Ile Thr Asn Thr Phe Thr Asn Leu
130                 135                 140

Glu Pro Gln Val Asp Glu Asn Trp Ile Val Trp Arg Asn Leu Ser Ala
145                 150                 155                 160

Thr His Thr Ser Tyr Tyr Lys Ile Leu Phe Ser Ile Gln Asn Glu
                165                 170                 175

Asp Thr Gly Ala Phe Met Ala Val Leu Pro Ile Ala Phe Glu Ile Thr
                180                 185                 190

Val Asp Val Gln Lys Gln Gln Leu Leu Phe Ile Thr Ile Arg Asp Ser
                195                 200                 205

Ala Arg Tyr Glu Val Lys Met Lys Ala Leu Thr Val Val Gln Leu Leu
            210                 215                 220

Asp Ser Tyr Asn Ala Pro Ile Ile Asp Val Phe Asn Val His Asn Tyr
225                 230                 235                 240

Gly Leu Tyr Gln Ser Asn His Pro Asn His Ile Leu Gln Asn Leu
                245                 250                 255

Asn Leu Asn Lys Ile Lys Gly
                260

<210> SEQ ID NO 12
<211> LENGTH: 260
<212> TYPE: PRT
<213> ORGANISM: Bacillus thuringiensis

<400> SEQUENCE: 12

Met Tyr Ile Asn Asn Phe Asp Phe Pro Glu Lys Asn Asn Asp Tyr Gln
1               5                   10                  15

Cys Ser Gly Pro Ile Ile Lys Lys Pro Phe Arg His Ile Ala Leu Thr
            20                  25                  30

Val Pro Ser Ser Asp Ile Thr Asn Phe Asn Glu Ile Phe Tyr Val Glu
        35                  40                  45

Pro Gln Tyr Ile Ala Gln Ala Leu Arg Leu Thr Asn Thr Phe Gln Gly
    50                  55                  60

Ala Ile Asp Pro Leu Thr Leu Asn Phe Asn Phe Glu Lys Ala Leu Gln
65                  70                  75                  80

Ile Ala Asn Gly Leu Pro Asn Ala Gly Val Thr Gly Thr Leu Asn Gln
                85                  90                  95

Ser Val Ile His Gln Thr Ile Glu Ile Ser Val Met Ile Ser Gln Ile
            100                 105                 110
```

```
Lys Glu Ile Ile Arg Ser Val Leu Gly Leu Val Ile Asn Ser Ala Asn
        115                 120                 125

Phe Trp Asn Asn Val Val Ser Ala Ile Thr Asn Thr Phe Thr Asn Leu
    130                 135                 140

Glu Pro Gln Val Asp Glu Asn Trp Ile Val Trp Arg Asn Leu Ser Ala
145                 150                 155                 160

Asn Gln Thr Ser Tyr Tyr Tyr Lys Ile Leu Phe Ser Ile Gln Asn Glu
                165                 170                 175

Asp Thr Gly Arg Phe Met Ala Val Leu Pro Ile Ala Phe Glu Ile Asn
            180                 185                 190

Val Asp Val His Lys Gln Gln Leu Leu Phe Ile Thr Ile Lys Asp Ser
        195                 200                 205

Ala Arg Tyr Glu Val Lys Met Lys Ala Leu Thr Val Val Gln Ala Leu
    210                 215                 220

Asp Ser Tyr Asn Ala Pro Ile Ile Asp Val Phe Asn Ile His Asn Tyr
225                 230                 235                 240

Ser Leu His Arg Pro Asn Tyr His Ile Leu Gln Asn Leu Asn Val Asn
                245                 250                 255

Pro Ile Lys Ser
            260

<210> SEQ ID NO 13
<211> LENGTH: 643
<212> TYPE: PRT
<213> ORGANISM: Bacillus thuringiensis

<400> SEQUENCE: 13

Met Glu Asp Ser Ser Leu Asp Thr Leu Ser Ile Val Asn Glu Thr Asp
1               5                   10                  15

Phe Pro Leu Tyr Asn Asn Tyr Thr Glu Pro Thr Ile Ala Pro Ala Leu
            20                  25                  30

Ile Ala Val Ala Pro Ile Ala Gln Tyr Leu Ala Thr Ala Ile Gly Lys
        35                  40                  45

Trp Ala Ala Lys Ala Ala Phe Ser Lys Val Leu Ser Leu Ile Phe Pro
    50                  55                  60

Gly Ser Gln Pro Ala Thr Met Glu Lys Val Arg Thr Glu Val Glu Thr
65                  70                  75                  80

Leu Ile Asn Gln Lys Leu Ser Gln Asp Arg Val Asn Ile Leu Asn Ala
                85                  90                  95

Glu Tyr Arg Gly Ile Ile Glu Val Ser Asp Val Phe Asp Ala Tyr Ile
            100                 105                 110

Lys Gln Pro Gly Phe Thr Pro Ala Thr Ala Lys Gly Tyr Phe Leu Asn
        115                 120                 125

Leu Ser Gly Ala Ile Ile Gln Arg Leu Pro Gln Phe Glu Val Gln Thr
    130                 135                 140

Tyr Glu Gly Val Ser Ile Ala Leu Phe Thr Gln Met Cys Thr Leu His
145                 150                 155                 160

Leu Thr Leu Leu Lys Asp Gly Ile Leu Ala Gly Ser Ala Trp Gly Phe
                165                 170                 175

Thr Gln Ala Asp Val Asp Ser Phe Ile Lys Leu Phe Asn Gln Lys Val
            180                 185                 190

Leu Asp Tyr Arg Thr Arg Leu Met Arg Met Tyr Thr Glu Glu Phe Gly
        195                 200                 205

Arg Leu Cys Lys Val Ser Leu Lys Asp Gly Leu Thr Phe Arg Asn Met
```

```
              210                 215                 220
Cys Asn Leu Tyr Val Phe Pro Phe Ala Glu Ala Trp Ser Leu Met Arg
225                 230                 235                 240

Tyr Glu Gly Leu Lys Leu Gln Ser Ser Leu Ser Leu Trp Asp Tyr Val
                245                 250                 255

Gly Val Ser Ile Pro Val Asn Tyr Asn Glu Trp Gly Gly Leu Val Tyr
            260                 265                 270

Lys Leu Leu Met Gly Glu Val Asn Gln Arg Leu Thr Thr Val Lys Phe
            275                 280                 285

Asn Tyr Ser Phe Thr Asn Glu Pro Ala Asp Ile Pro Ala Arg Glu Asn
290                 295                 300

Ile Arg Gly Val His Pro Ile Tyr Asp Pro Ser Ser Gly Leu Thr Gly
305                 310                 315                 320

Trp Ile Gly Asn Gly Arg Thr Asn Asn Phe Asn Phe Ala Asp Asn Asn
                325                 330                 335

Gly Asn Glu Ile Met Glu Val Arg Thr Gln Thr Phe Tyr Gln Asn Pro
            340                 345                 350

Asn Asn Glu Pro Ile Ala Pro Arg Asp Ile Ile Asn Gln Ile Leu Thr
            355                 360                 365

Ala Pro Ala Pro Ala Asp Leu Phe Phe Lys Asn Ala Asp Ile Asn Val
370                 375                 380

Lys Phe Thr Gln Trp Phe Gln Ser Thr Leu Tyr Gly Trp Asn Ile Lys
385                 390                 395                 400

Leu Gly Thr Gln Thr Val Leu Ser Ser Arg Thr Gly Thr Ile Pro Pro
                405                 410                 415

Asn Tyr Leu Ala Tyr Asp Gly Tyr Tyr Ile Arg Ala Ile Ser Ala Cys
            420                 425                 430

Pro Arg Gly Val Ser Leu Ala Tyr Asn His Asp Leu Thr Thr Leu Thr
            435                 440                 445

Tyr Asn Arg Ile Glu Tyr Asp Ser Pro Thr Thr Glu Asn Ile Ile Val
450                 455                 460

Gly Phe Ala Pro Asp Asn Thr Lys Asp Phe Tyr Ser Lys Lys Ser His
465                 470                 475                 480

Tyr Leu Ser Glu Thr Asn Asp Ser Tyr Val Ile Pro Ala Leu Gln Phe
                485                 490                 495

Ala Glu Val Ser Asp Arg Ser Phe Leu Glu Asp Thr Pro Asp Gln Ala
            500                 505                 510

Thr Asp Gly Ser Ile Lys Phe Ala Arg Thr Phe Ile Ser Asn Glu Ala
            515                 520                 525

Lys Tyr Ser Ile Arg Leu Asn Thr Gly Phe Asn Thr Ala Thr Arg Tyr
530                 535                 540

Lys Leu Ile Ile Arg Val Arg Val Pro Tyr Arg Leu Pro Ala Gly Ile
545                 550                 555                 560

Arg Val Gln Ser Gln Asn Ser Gly Asn Asn Arg Met Leu Gly Ser Phe
                565                 570                 575

Thr Ala Asn Ala Asn Pro Glu Trp Val Asp Phe Val Thr Asp Ala Phe
            580                 585                 590

Thr Phe Asn Asp Leu Gly Ile Thr Thr Ser Ser Thr Asn Ala Leu Phe
            595                 600                 605

Ser Ile Ser Ser Asp Ser Leu Asn Ser Gly Glu Glu Trp Tyr Leu Ser
610                 615                 620

Gln Leu Phe Leu Val Lys Glu Ser Ala Phe Thr Thr Gln Ile Asn Pro
625                 630                 635                 640
```

Leu Leu Lys

<210> SEQ ID NO 14
<211> LENGTH: 747
<212> TYPE: DNA
<213> ORGANISM: Artificial Sequence
<220> FEATURE:
<223> OTHER INFORMATION: Cyt1Aa variant

<400> SEQUENCE: 14

```
atggaaaatt taaatcattg tccattagaa gatataaagg taaatccatg gaaaacccct      60
caatcaacag caaggttat tacattacgt gttgaggatc caaatgaaat caataatctt     120
ctttctatta acgaaattga taatccgaat tatatattgc aagcaattat ggaagcaaat     180
gcatttcaaa atgcattagt tcccacttct acagattttg gtgatgccct acgctttagt     240
atgccaaaag gtttagaaat cgcaaacaca attacaccga tgggtgctgt agtgagttat     300
gttgatcaaa atgtaactca acgaataac caagtaagtg ttatgattaa taaagtctta     360
gaagtgttaa aaactgtatt aggagttgca ttaagtggat ctgtaataga tcaattaact     420
gcagcagtta caaatacgtt tacaaattta aatactcaaa aaatgaagc atggattttc     480
tggggcaagg aaactgctaa tcaaacaaat tacacataca atgtcctgtt tgcaatccaa     540
aatgcccaaa ctggtggcgt tatgtattgt gtaccagttg gttttgaaat taaagtatca     600
gcagtaaagg aacaagtttt attttttcaca attcaagatt ctgcgagcta caatgttaac     660
atccaatctt tgaaatttgc acaaccatta gttagctcaa gtcagtatcc aattgcagat     720
cttactagcg ctattaatgg aaccctc                                         747
```

<210> SEQ ID NO 15
<211> LENGTH: 249
<212> TYPE: PRT
<213> ORGANISM: Artificial Sequence
<220> FEATURE:
<223> OTHER INFORMATION: Cyt1Aa variant

<400> SEQUENCE: 15

```
Met Glu Asn Leu Asn His Cys Pro Leu Glu Asp Ile Lys Val Asn Pro
  1               5                  10                  15

Trp Lys Thr Pro Gln Ser Thr Ala Arg Val Ile Thr Leu Arg Val Glu
             20

```
Trp Gly Lys Glu Thr Ala Asn Gln Thr Asn Tyr Thr Tyr Asn Val Leu
            165                 170                 175
Phe Ala Ile Gln Asn Ala Gln Thr Gly Gly Val Met Tyr Cys Val Pro
            180                 185                 190
Val Gly Phe Glu Ile Lys Val Ser Ala Val Lys Glu Gln Val Leu Phe
            195                 200                 205
Phe Thr Ile Gln Asp Ser Ala Ser Tyr Asn Val Asn Ile Gln Ser Leu
            210                 215                 220
Lys Phe Ala Gln Pro Leu Val Ser Ser Gln Tyr Pro Ile Ala Asp
225                 230                 235                 240
Leu Thr Ser Ala Ile Asn Gly Thr Leu
            245
```

<210> SEQ ID NO 16
<211> LENGTH: 747
<212> TYPE: DNA
<213> ORGANISM: Artificial Sequence
<220> FEATURE:
<223> OTHER INFORMATION: Cyt1Aa variant

<400> SEQUENCE: 16

```
atggaaaatt taaatcattg tccattagaa gatataaagg taaatccatg gaaaacccct      60
caatcaacag caagggttat tacattacgt gttgaggatc caatgaaat caataatctt     120
ctttctatta cgaaattga taatccgaat tatatattgc aagcaattat gttagaaaat     180
gcatttcaaa atgcattagt tcccacttct acagattttg gtgatgccct acgctttagt     240
atgccaaaag gtttagaaat cgcaaacaca attacaccga tgggtgctgt agtgagttat     300
gttgatcaaa atgtaactca aacgaataac caagtaagtg ttatgattaa taaagtctta     360
gaagtgttaa aaactgtatt aggagttgca ttaagtggat ctgtaataga tcaattaact     420
gcagcagtta caaatacgtt tacaaattta aatactcaaa aaaatgaagc atggatttc     480
tggggcaagg aaactgctaa tcaaacaaat tacacataca atgtcctgtt tgcaatccaa     540
aatgcccaaa ctggtggcgt tatgtattgt gtaccagttg gttttgaaat taagtatca     600
gcagtaaagg aacaagtttt atttttcaca attcaagatt ctgcgagcta caatgttaac     660
atccaatctt tgaaatttgc acaaccatta gttagctcaa gtcagtatcc aattgcagat     720
cttactagcg ctattaatgg aaccctc                                          747
```

<210> SEQ ID NO 17
<211> LENGTH: 249
<212> TYPE: PRT
<213> ORGANISM: Artificial Sequence
<220> FEATURE:
<223> OTHER INFORMATION: Cyt1Aa variant

<400> SEQUENCE: 17

```
Met Glu Asn Leu Asn His Cys Pro Leu Gl

```
Met Pro Lys Gly Leu Glu Ile Ala Asn Thr Ile Thr Pro Met Gly Ala
                 85                  90                  95

Val Val Ser Tyr Val Asp Gln Asn Val Thr Gln Thr Asn Asn Gln Val
            100                 105                 110

Ser Val Met Ile Asn Lys Val Leu Glu Val Leu Lys Thr Val Leu Gly
        115                 120                 125

Val Ala Leu Ser Gly Ser Val Ile Asp Gln Leu Thr Ala Ala Val Thr
    130                 135                 140

Asn Thr Phe Thr Asn Leu Asn Thr Gln Lys Asn Glu Ala Trp Ile Phe
145                 150                 155                 160

Trp Gly Lys Glu Thr Ala Asn Gln Thr Asn Tyr Thr Tyr Asn Val Leu
                165                 170                 175

Phe Ala Ile Gln Asn Ala Gln Thr Gly Gly Val Met Tyr Cys Val Pro
            180                 185                 190

Val Gly Phe Glu Ile Lys Val Ser Ala Val Lys Glu Gln Val Leu Phe
        195                 200                 205

Phe Thr Ile Gln Asp Ser Ala Ser Tyr Asn Val Asn Ile Gln Ser Leu
    210                 215                 220

Lys Phe Ala Gln Pro Leu Val Ser Ser Ser Gln Tyr Pro Ile Ala Asp
225                 230                 235                 240

Leu Thr Ser Ala Ile Asn Gly Thr Leu
                245
```

<210> SEQ ID NO 18
<211> LENGTH: 747
<212> TYPE: DNA
<213> ORGANISM: Artificial Sequence
<220> FEATURE:
<223> OTHER INFORMATION: Cyt1Aa variant

<400> SEQUENCE: 18

```
atggaaaatt taaatcattg tccattagaa gatataaagg taaatccatg gaaaacccct      60
caatcaacag caagggttat tacattacgt gttgaggatc caaatgaaat caataatctt     120
ctttctatta cgaaattga taatccgaat tatatattgc aagcaattat gttagcaaat     180
gcacggcaaa atgcattagt tcccacttct acagattttg gtgatgccct acgctttagt     240
atgccaaaag gtttagaaat cgcaaacaca attacaccga tgggtgctgt agtgagttat     300
gttgatcaaa atgtaactca acgaataac caagtaagtg ttatgattaa taagtcttat         360
gaagtgttaa aaactgtatt aggagttgca ttaagtggat ctgtaataga tcaattaact     420
gcagcagtta caaatacgtt tacaaattta atactcaaa aaaatgaagc atggattttc       480
tggggcaagg aaactgctaa tcaaacaaat tacacataca atgtcctgtt tgcaatccaa     540
aatgcccaaa ctggtggcgt tatgtattgt gtaccagttg gttttgaaat taagtatca       600
gcagtaaagg aacaagtttt attttcaca attcaagatt ctgcgagcta caatgttaac       660
atccaatctt tgaaatttgc acaaccatta gttagctcaa gtcagtatcc aattgcagat     720
cttactagcg ctattaatgg aaccctc                                         747
```

<210> SEQ ID NO 19
<211> LENGTH: 249
<212> TYPE: PRT
<213> ORGANISM: Artificial Sequence
<220> FEATURE:
<223> OTHER INFORMATION: Cyt1Aa -continued

```
Met Glu Asn Leu Asn His Cys Pro Leu Glu Asp Ile Lys Val Asn Pro
1               5                   10                  15

Trp Lys Thr Pro Gln Ser Thr Ala Arg Val Ile Thr Leu Arg Val Glu
            20                  25                  30

Asp Pro Asn Glu Ile Asn Asn Leu Leu Ser Ile Asn Glu Ile Asp Asn
        35                  40                  45

Pro Asn Tyr Ile Leu Gln Ala Ile Met Leu Ala Asn Ala Arg Gln Asn
    50                  55                  60

Ala Leu Val Pro Thr Ser Thr Asp Phe Gly Asp Ala Leu Arg Phe Ser
65                  70                  75                  80

Met Pro Lys Gly Leu Glu Ile Ala Asn Thr Ile Thr Pro Met Gly Ala
                85                  90                  95

Val Val Ser Tyr Val Asp Gln Asn Val Thr Gln Thr Asn Asn Gln Val
            100                 105                 110

Ser Val Met Ile Asn Lys Val Leu Glu Val Leu Lys Thr Val Leu Gly
        115                 120                 125

Val Ala Leu Ser Gly Ser Val Ile Asp Gln Leu Thr Ala Ala Val Thr
    130                 135                 140

Asn Thr Phe Thr Asn Leu Asn Thr Gln Lys Asn Glu Ala Trp Ile Phe
145                 150                 155                 160

Trp Gly Lys Glu Thr Ala Asn Gln Thr Asn Tyr Thr Tyr Asn Val Leu
                165                 170                 175

Phe Ala Ile Gln Asn Ala Gln Thr Gly Val Met Tyr Cys Val Pro
            180                 185                 190

Val Gly Phe Glu Ile Lys Val Ser Ala Val Lys Glu Gln Val Leu Phe
    195                 200                 205

Phe Thr Ile Gln Asp Ser Ala Ser Tyr Asn Val Asn Ile Gln Ser Leu
210                 215                 220

Lys Phe Ala Gln Pro Leu Val Ser Ser Gln Tyr Pro Ile Ala Asp
225                 230                 235                 240

Leu Thr Ser Ala Ile Asn Gly Thr Leu
                245
```

<210> SEQ ID NO 20
<211> LENGTH: 38
<212> TYPE: DNA
<213> ORGANISM: Artificial Sequence
<220> FEATURE:
<223> OTHER INFORMATION: mutagenesis primer

<400> SEQUENCE: 20
ttgcaagcaa ttatgttatg taatgccttt caaaatgc                           38

<210> SEQ ID NO 21
<211> LENGTH: 46
<212> TYPE: DNA
<213> ORGANISM: Artificial Sequence
<220> FEATURE:
<223> OTHER INFORMATION: mutagenesis primer

<400> SEQUENCE: 21
gcaagcaatt atgttagcaa actgttttca aaatgcatta gttccc                  46

<210> SEQ ID NO 22
<211> LENGTH: 44
<212> TYPE: DNA
<213> ORGANISM: Artificial Sequence
<220> FEATURE:
<223> OTHER INFORMATION: mutagenesis primer

```
<400> SEQUENCE: 22
tatatattgc aagcaattat ggaagcaaat gcgtttcaaa atgc                          44

<210> SEQ ID NO 23
<211> LENGTH: 42
<212> TYPE: DNA
<213> ORGANISM: Artificial Sequence
<220> FEATURE:
<223> OTHER INFORMATION: mutagenesis primer

<400> SEQUENCE: 23
tatattgcaa gcaattatgt tagaaaatgc gtttcaaaat gc                            42

<210> SEQ ID NO 24
<211> LENGTH: 42
<212> TYPE: DNA
<213> ORGANISM: Artificial Sequence
<220> FEATURE:
<223> OTHER INFORMATION: mutagenesis primer

<400> SEQUENCE: 24
agcaattatg ttagcaaatg cacggcaaaa tgcgttagtt cc                            42

<210> SEQ ID NO 25
<211> LENGTH: 29
<212> TYPE: DNA
<213> ORGANISM: Artificial Sequence
<220> FEATURE:
<223> OTHER INFORMATION: mutagenesis primer

<400> SEQUENCE: 25
tgtgaattca tggaaaattt aaatcattg                                           29

<210> SEQ ID NO 26
<211> LENGTH: 27
<212> TYPE: DNA
<213> ORGANISM: Artificial Sequence
<220> FEATURE:
<223> OTHER INFORMATION: mutagenesis primer

<400> SEQUENCE: 26
ctactcgagg agggttccat taatagc                                             27
```

That which is claimed:

1. A Cyt1A variant polypeptide comprising an amino acid substitution at a residue corresponding to position 59 and/or 61 of SEQ ID NO: 2, wherein the Cyt1A variant polypeptide has decreased hemolytic activity compared to the Cyt1A polypeptide of SEQ ID NO: 2, and has at least 95% sequence identity to SEQ ID NO: 2.

2. The Cyt1A variant polypeptide of claim 1, wherein the amino acid substitution at position 59 or 61 is cysteine.

3. The Cyt1A variant polypeptide of claim 1 or 2, wherein the Cyt1A variant polypeptide has at least 95% identity to SEQ ID NO: 4 or SEQ ID NO: 6.

4. The Cyt1A variant polypeptide of claim 1, or wherein the Cyt1A variant polypeptide comprises an amino acid sequence selected from SEQ ID NO: 4 and SEQ ID NO: 6.

5. The Cyt1A variant polypeptide of claim 1, wherein the hemolytic activity is expressed as an $ED_{50}$ against rabbit red blood cells.

6. The Cyt1A variant polypeptide of claim 5, wherein the hemolytic activity is decreased at least 4 fold compared to the Cyt1A polypeptide of SEQ ID NO: 2.

7. A recombinant nucleic acid molecule encoding the Cyt1A variant polypeptide of claim 1.

8. The recombinant nucleic acid molecule of claim 7, where in the nucleic acid sequence has been optimized for expression in a plant.

9. The recombinant nucleic acid molecule of claim 8, where in the nucleic acid sequence is a synthetic nucleotide sequence having plant preferred codons that have been designed for expression in a plant.

10. The recombinant nucleic acid molecule of claim 7, wherein the nucleic acid is selected from SEQ ID NO: 3 and SEQ ID NO: 7.

11. A DNA construct comprising the nucleic acid molecule of claim 7 and a heterologous regulatory element operably linked to the nucleic acid molecule.

12. A host cell comprising the DNA construct of claim 11.

13. The host cell of claim 12, wherein the host cell is a bacterial cell.

14. A composition comprising the Cyt1A variant polypeptide of claim 1.

15. The composition of claim 14, wherein the composition comprises from 1% to 99% by weight of said polypeptide.

16. A method for producing a Cyt1A variant polypeptide with decreased hemolytic activity, comprising culturing the host cell of claim 12 under conditions in which the nucleic acid molecule encoding the Cyt1A variant polypeptide is expressed.

17. A method of controlling a Dipteran pest species, comprising contacting the Dipteran pest species with the composition of claim 14.

18. The method of claim 17, wherein the Dipteran pest is in the Genus *Aedes, Culex* or *Anopheles*.

19. The method of claim 18, wherein the Dipteran pest is *Aedes aegypti, Culex quinquefasciatus* or *Anopheles gambiae*.

20. The Cyt1A variant polypeptide of claim 1, wherein the Cyt1A variant polypeptide is SEQ ID NO: 2 comprising an amino acid substitution at a residue corresponding to position 59 and/or 61.

* * * * *